US006303818B1

United States Patent
Zhang et al.

(10) Patent No.: US 6,303,818 B1
(45) Date of Patent: Oct. 16, 2001

(54) UNSATURATED OXIME ETHERS AND THEIR USE AS FUNGICIDES

(75) Inventors: Lixin Zhang, Shenyang (CN); Steven Howard Shaber, Horsham, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/634,649

(22) Filed: Aug. 8, 2000

(51) Int. Cl.[7] ............ C07C 233/00; C07C 327/00; C07C 261/00; C07C 249/00; C07D 239/02
(52) U.S. Cl. ............ 564/163; 558/256; 560/35; 562/440; 504/147; 544/335; 544/336; 546/329; 548/214
(58) Field of Search ............ 558/256; 560/35; 562/440; 564/163; 504/147; 544/335, 336; 546/329; 548/214

(56) References Cited

U.S. PATENT DOCUMENTS 5,563,168 * 10/1996 Brand et al. ............ 514/357

OTHER PUBLICATIONS

Brand et al, o–Benzyl oximes, their preparation, and fungicides/pesticides containing them, Caplus AN: 1992: 151325, p. 38.*

* cited by examiner

Primary Examiner—Johann Richter
Assistant Examiner—J. Parsa
(74) Attorney, Agent, or Firm—Thomas D. Rogerson

(57) ABSTRACT

The present invention relates to certain oxime ether compounds, compositions containing these compounds, and methods for controlling fungi by the use of a fungitoxic amount of the compounds or compositions.

10 Claims, No Drawings

UNSATURATED OXIME ETHERS AND THEIR USE AS FUNGICIDES

The present invention relates to certain oxime ether compounds, compositions containing these compounds, and methods for controlling fungi by the use of a fungitoxic amount of the compounds or compositions.

Compounds having certain oxime ether structures are disclosed in U.S. Pat. No. 5,055,471 are useful as fungicides. We have discovered new oxime ether structures which possess a substituted alkenyl moiety which possess broad spectrum fungicidal properties.

The oxime ethers of the present invention have the Formula (I)

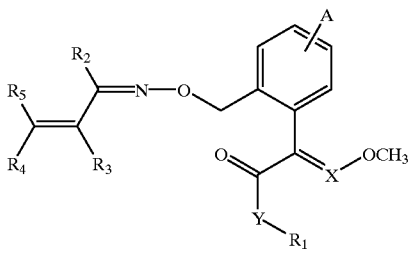

wherein X is N or CH; Y is O, S, or $NR_6$;

A is hydrogen, halo, cyano, $(C_1-C_{12})$alkyl, or $(C_1-C_{12})$alkoxy;

$R_1$ and $R_6$ are independently hydrogen or $(C_1-C_4)$alkyl;

$R_2$ is hydrogen, $(C_1-C_{12})$alkyl, halo$(C_1-C_{12})$alkyl, $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, cyano, aryl, aralkyl, heterocyclic, or heterocyclic$(C_1-C_4)$alkyl;

$R_3$ is hydrogen or $(C_1-C_4)$alkyl;

$R_4$ and $R_5$ are independently hydrogen, $(C_1-C_4)$alkyl, aryl, aralkyl, aryl$(C_2-C_8)$alkenyl, aryl$(C_2-C_8)$alkynyl, heterocyclic, or heterocyclic$(C_1-C_4)$alkyl, wherein in each aryl, aralkyl, aryl$(C_2-C_8)$alkenyl, aryl$(C_2-C_8)$alkynyl, heterocyclic or heterocyclic$(C_1-C_4)$alkyl the aryl or heterocyclic ring is substituted with from 2 to 5 substituents and wherein the positions on the aryl or heterocyclic ring adjacent to the ethylenic bond, in Formula I, are both substituted and wherein if one of $R_4$ and $R_5$ is hydrogen or $(C_1-C_4)$alkyl then the other of $R_4$ and $R_5$ is other than hydrogen or $(C_1-C_4)$alkyl.

The aforementioned $(C_1-C_4)$alkyl, $(C_1-C_{12})$alkyl, $(C_2-C_8)$alkenyl, $(C_2-C_8)$alkynyl and $(C_3-C_7)$cycloalkyl groups may be optionally substituted with up to three substituents selected from the group consisting of nitro, halomethyl, $(C_1-C_4)$alkoxycarbonyl, and cyano.

The term alkyl includes both branched and straight chain alkyl groups containing from 1 to 12 carbon atoms. Typical alkyl groups include for example, methyl, ethyl, n-propyl, iso-propyl, n-butyl, sec-butyl, isobutyl, t-butyl, n-pentyl, isopentyl, n-hexyl, n-heptyl, isooctyl, nonyl, decyl, undecyl, and dodecyl. The term haloalkyl refers to an alkyl group substituted with 1 to 3 halogens.

The term alkenyl refers to an ethylenically unsaturated hydrocarbon group, straight or branched, having a chain length of 2 to 8 carbon atoms and 1 or 2 ethylenic bonds. The term haloalkenyl refers to an alkenyl group substituted with 1 to 3 halogen atoms. The term alkynyl refers to an unsaturated hydrocarbon group, straight or branched, having a chain length of 2 to 12 carbon atoms and I or 2 acetylenic bonds.

The term aryl includes phenyl and naphthyl which maybe substituted with up to five substituents independently selected from halogen, cyano, nitro, trihalomethyl, phenyl, phenoxy, $(C_1-C_4)$alkyl, $(C_1-C_4)$alkoxy, $(C_1-C_4)$alkylthio, $(C_1-C_4)$alkylsulfoxide, halo$(C_1-C)$alkyl, halo$(C_1-C_4)$alkoxy, halo$(C_2-C_8)$alkenyl, halo$(C_2-C_8)$alkynyl, heterocyclic, phenoxy, $(C_1-C_4)$alkylamino, $(C_1-C_4)$dialkylamino, and phenyl. Each aryl may be substituted with one or more substituents independently selected from halogen, cyano, trihalomethyl, phenyl, phenoxy$(C_1-C_4)$alkyl, $(C_1-C_4)$alkoxy and $(C_1-C_4)$alkylthio, Typical phenyl substituents, where both positions on the phenyl ring adjacent to the ethylenic bond, in Formula I, are substituted include, for example 2,6-dichloro, 2,3,6-trichloro, 2,4,6-trichloro, 2,6-difluoro, 2,3,6-trifluoro, 2,4,6-trifluoro, 2,6-dibromo, 2,3,6-tribromo, 2,4,6-tribromo, 2,3,4,6-tetrachloro, 2,3,5,6-tetrachloro, 2,3,4,5,6-pentachloro, 2,3,4,6-tetrabromo, 2,3,5,6-tetrabromo, 2,3,4,5,6-pentabromo, 2,3,4,6-tetrafluoro, 2,3,5,6-tetrafluoro, 2,3,4,5,6-pentafluoro, 2,6-dimethyl, 2,3,6-trimethyl, 2,4,6-trimethyl, 2,6-dimethoxy, 2,3,6-trimethoxy, 2,4,6-trimethoxy, 2,6-triethoxy, 2,3,6-triethoxy, 2,4,6-triethoxy, 2, 3,4,6-tetramethyl, 2,3,5,6-tetramethyl, 2,3,4,5,6-pentaxiiethyl, 2,3,4,6-tetramethoxy, 2,3,5,6-tetramethoxy, 2,3,4,5,6-pentamethoxy, 2,3,4,6-tetraethoxy, 2,3,5,6-tetraethoxy, 2,3,4,5,6-pentaethoxy, 2,6-dicyano, 2,3,6-tricyano, 2,4,6-tricyano, 2,6-diphenyl, 2,6-diphenoxy, 2,6-dibenzyl, 2,6-bis(trifluoromethyl), 2,3,6-tris-(trifluoromethyl), 2,4,6-tris-(trifluoromethyl), 2,3,4,5-tetra-(trifluoromethyl), 2,3,4,6-tetra-(trifluoromethyl), 2,3,5,6-tetra-(trifluoromethyl), 2,3,4,5,6-penta-(trifluoromethyl), 2,6-bis-(trifluoromethoxy), 2,3,6-tris(trifluoromethoxy), 2,4,6-tri-(trifluoromethoxy), 2,3,4,5-tetra-(trifluoromethoxy), 2,3,4,6-tetra-(trifluoromethoxy), 2,3,5,6-tetra-(trifluoromethoxy), 2,3,4,5,6-penta-(trifluoromethoxy), 2-bromo-6-chloro, 2-bromo-6-fluoro, 2-bromo-6-(trifluoromethyl), 2-bromo-6-(trifluoromethoxy), 2-bromo-6-cyano, 2-chloro-6-fluoro, 2-chloro-6-(trifluoromethyl), 2-chloro-6-methyl, 2-chloro-6-(trifluoromethoxy), 2-chloro-6-cyano, 2-fluoro-6-(trifluoromethyl), 2-fluoro-6-methyl 2-fluoro-6-(trifluoromethoxy).

The term heterocyclic refers to a substituted 6 membered unsaturated ring selected from 3-pridinyl, 4-pyridinyl, 5-pyrimidinyl, 3-pyridazinyl or a 5 membered unsaturated ring selected from 3-thienyl, 3-furyl, 3-pyrrolyl, 4-isoxazolyl, 4-isothiazolyl and 4-pyrazolyl wherein both the positions on the heterocyclic ring adjacent to the ethylenic bond in Formula I are substituted and the ring is substituted with from 2 to 4 substituents independently selected from $(C_1-C_4)$ alkyl, $(C_3-C_7)$cycloalkyl, trihalomethyl, trihalomethoxy, halogen, cyano, $(C_1-C_4)$alkoxycarbonyl, nitro, phenyl, and phenoxy.

The term arylalkyl is used to describe a group wherein the alkyl chain is from 1 to 10 carbon atoms and can be a branched or straight chain, preferably a straight chain, with the aryl portion as defined above, forming a terminal portion of the arylalkyl moiety. Typical arylalkyl moieties are optionally substituted benzyl, phenethyl, phenpropyl, and phenbutyl moieties. Typical benzyl moieties wherein both positions on the phenyl ring, adjacent to the methylene which is bonded to the ethylenic bond in formula I, are substituted include, for example 2,6-dichlorobenzyl, 2,3,6-trichlorobenzyl, 2,4,6-trichlorobenzyl, 2,6-difluorobenzyl, 2,3,6-fluorobenzyl, 2,4,6-trifluorobenzyl, 2,6-bis(trifluoromethyl)benzyl, 2,3,6-tris(trifluoromethyl)benzyl, 2,4,6-tris(trifluoromethyl)benzyl, 2,3,4,6-tetrachlorobenzyl, 2,3,5,6-tetrachlorobenzyl, 2,3,4,5,6-pentachlorobenzyl, 2,3, 4,6-tetrabromobenzyl, 2,3,5,6-tetrabromobenzyl, 2,3,4,5,6-pentabromobenzyl, 2,3,4,6-tetrafluorobenzyl, 2,3,5,6-tetrafluorobenzyl, and 2,3,4,5,6-pentafluorobenzyl. Typical phenethyl moieties wherein both positions on the phenyl ring, adjacent to the ethyl moiety which is bonded to the ethylenic bond in Formula I, are substituted include, for example 2-(2,6-dichlorophenyl)ethyl, 2-(2,3,6-trichlorophenyl)ethyl, 2-(2,4,6-trichlorophenyl)-ethyl, 2-(2,6-difluorophenyl)ethyl, 2-(2,3,6-trifluorophenyl)ethyl, 2-(2,4,6-trifluorophenyl)ethyl, 2-(2,6-dimethylphenyl)ethyl, 2-(2,3,6-trimethylphenyl)-ethyl, 2-(2,4,6-trimethylphenyl)ethyl, 2-(2,6-bis-(trifluoromethyl)-phenyl)ethyl, 2-(2,3,6-tris(trifluoromethyl)-phenyl)ethyl 2-(2,4,6-tris(trifluoromethyl)-phenyl)ethyl, 2-(2,6-dimethoxyphenyl)ethyl, 2-(2,3,6-trimethoxy-phenyl)ethyl, and 2-(2,4,6-trimethoxyphenyl)ethyl. Typical phenpropyl moieties wherein both positions on the phenyl ring, adjacent to the propyl moiety which is bonded to ethylenic bond in Formula I, are substituted include, for example 3(2,6-dichlorophenyl)propyl, 3-(2,3,6-trichlorophenyl)propyl, 3-(2,4,6-trichlorophenyl)propyl, 3-(2,6-difluorophenyl)propyl, 3-(2,3,6-trifluorophenyl)-propyl, 3-(2,4,6-trifluorophenyl)propyl, 3-(2,6-dimethylphenyl)propyl, 3-(2,3,6-trimethyl-phenyl)propyl, 3-(2,4,6-trimethylphenyl)propyl and 3-(2,6-bis(trifluoromethyl)-phenyl)propyl. Typical phenbutyl moieties wherein both positions on the phenyl ring, adjacent to the butyl moiety which is bonded to ethylenic bond in Formula I, are substituted include, for example 4-(2,6-dichlorophenyl)butyl, 4-(2,3,6-trichlorophenyl)butyl, 4-(2,4,6-trichlorophenyl)butyl, 4-(2,6-difluorophenyl)butyl, 4-(2,3,6-trifluorophenyl)butyl, 4-(2,4,6-trifluorophenyl)butyl, 4-(2,6-dimethylphenyl)butyl, 4-(2,3,6-trimethylphenyl)butyl, 4-(2,4,6-trimethylphenyl)butyl and 4-(2,6-bis(trifluoromethyl) phenyl)butyl.

Halogen or halo is meant to include iodo, fluoro, bromo and chloro moieties.

Because of the C=C or C=N double bonds, the compounds of the general Formula I may be obtained in preparation as E/Z isomeric mixtures. These isomers can be separated into individual components by conventional means. The alkenes of Formula I may be obtained in preparation as cis and trans isomeric mixtures which can be separated into individual components by conventional means. Both the individual isomeric compounds and mixtures thereof form subjects of the invention and can be used as fungicides.

The present invention also includes the enantiomorphs, salts and complexes of Formula (1).

A preferred embodiment of this invention includes the compounds, enantiomorphs, salts and complexes of Formula I wherein X is CH or N; Y is O or NH; A is hydrogen; $R_1$ is $(C_1–C_4)$alkyl; $R_3$ and $R_5$ are hydrogen; $R_2$ is hydrogen or $(C_1–C_{12})$alkyl; and $R_4$ is 2,6-disubstitutedphenyl, 2,3,6-trisubstitutedphenyl, 2,4,6-trisubstitutedphenyl, 2,3,4,6-tetrasubstitutedphenyl, 2,3,5,6-tetrasubstituted, or 2,3,4,5,6-pentasubstitutedphenyl.

Another preferred embodiment of this invention includes the compounds, enantiomorphs, salts and complexes of Formula I wherein X is CH or N; Y is O or NH, A is hydrogen; $R_1$ is $(C_1–C_4)$alkyl; $R_3$ and $R_5$ are hydrogen; $R_2$ is hydrogen or $(C_1–C_{12})$alkyl; and $R_4$ is 2,6-dihalophenyl, 2,3,6-trihalophenyl, 2,4,6-trihalophenyl, 2,3,4,6-tetrahalophenyl, 2,3,5,6-tetrahalophenyl, or 2,3,4,5,6-pentahalophenyl.

A more preferred embodiment of this invention includes the compounds, enantiomorphs, salts and complexes of Formula I wherein X is N; Y is NH, A is hydrogen; $R_1$ is $CH_3$; $R_3$ and $R_5$ are hydrogen; $R_2$ is hydrogen or $(C_1–C_{12})$alkyl; and $R_4$ is 2,6-halophenyl, 2,3,6-trihalophenyl, or 2,4,6-trihalophenyl, An even more preferred embodiment of this invention includes the compounds, enantiomorphs, salts and complexes of Formula I wherein X is N; Y is NH, A is hydrogen; $R_1$ and $R_2$ are $CH_3$; $R_3$ and $R_5$ are hydrogen; and $R_4$ is 2,6-dichlorophenyl, 2,6-difluorophenyl, 2-chloro-6-fluoro, 2,3,6-trichlorophenyl, or 2,4,6-trichlorophenyl, A most preferred embodiment of this invention is the compound, enantiomorphs, salts and complexes of Formula I':

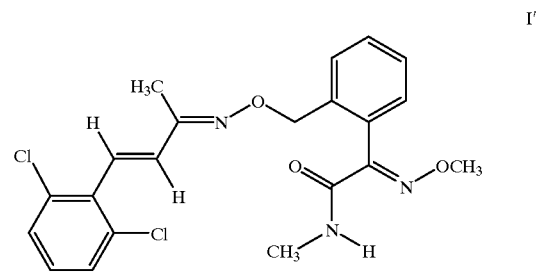

I'

Typical compounds of Formula I encompassed by the present invention wherein Y is O and X is CH are compounds of Formula IV wherein A, $R_3$, and $R_5$ are hydrogen; including those compounds of Formula IV' presented in Table 1 where $R_2$ and $R_4$ are as defined in Table 1.

TABLE 1

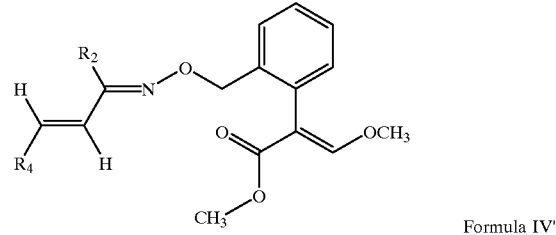

Formula IV'

| Compd # | $R_2$ | $R_4$ |
|---|---|---|
| 1.1 | H | 2,6-Cl(Ph) |
| 1.2 | H | 2,3,6-Cl(Ph) |
| 1.3 | H | 2,4,6-Cl(Ph) |
| 1.4 | H | 2,6-Br(Ph) |
| 1.5 | H | 2,3,6-Br(Ph) |
| 1.6 | H | 2,4,6-Br(Ph) |
| 1.7 | H | 2,6-F(Ph) |
| 1.8 | H | 2,3,6-F(Ph) |
| 1.9 | H | 2,4,6-F(Ph) |
| 1.10 | H | 2,6-$CH_3$(Ph) |
| 1.11 | H | 2,3,6-$CH_3$(Ph) |
| 1.12 | H | 2,4,6-$CH_3$(Ph) |
| 1.13 | H | 2,6-$CH_3O$(Ph) |
| 1.14 | H | 2,3,6-$CH_3O$(Ph) |
| 1.15 | H | 2,4,6-$CH_3O$(Ph) |
| 1.16 | $CH_3$ | 2,6-Cl(Ph) |
| 1.17 | $CH_3$ | 2,3,6-Cl(Ph) |
| 1.18 | $CH_3$ | 2,4,6-Cl(Ph) |
| 1.19 | $CH_3$ | 2,6-Br(Ph) |
| 1.20 | $CH_3$ | 2,3,6-Br(Ph) |
| 1.21 | $CH_3$ | 2,4,6-Br(Ph) |
| 1.22 | $CH_3$ | 2,6-F(Ph) |
| 1.23 | $CH_3$ | 2,3,6-F(Ph) |
| 1.24 | $CH_3$ | 2,4,6-F(Ph) |
| 1.25 | $CH_3$ | 2,6-$CH_3$(Ph) |
| 1.26 | $CH_3$ | 2,3,6-$CH_3$(Ph) |
| 1.27 | $CH_3$ | 2,4,6-$CH_3$(Ph) |

TABLE 1-continued

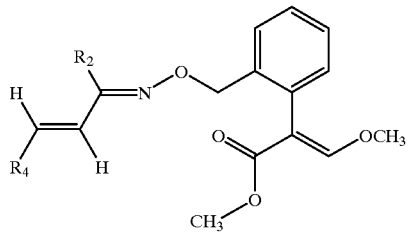

Formula IV'

| Compd # | R$_2$ | R$_4$ |
|---|---|---|
| 1.28 | CH$_3$ | 2,6-CH$_3$O(Ph) |
| 1.29 | CH$_3$ | 2,3,6-CH$_3$O(Ph) |
| 1.30 | CH$_3$ | 2,4,6-CH$_3$O(Ph) |
| 1.31 | CH$_3$ | 2,6-NO$_2$(Ph) |
| 1.32 | CH$_3$ | 2,6-CN(Ph) |
| 1.33 | CH$_3$ | 2,3,6-CN(Ph) |
| 1.34 | CH$_3$ | 2,4,6-CN(Ph) |
| 1.35 | CH$_3$ | 2,6-Ph(Ph) |
| 1.36 | CH$_3$ | 2,3,6-Ph(Ph) |
| 1.37 | CH$_3$ | 2,4,6-Ph(Ph) |
| 1.38 | CH$_3$ | 2,6-PhO(Ph) |
| 1.39 | CH$_3$ | 2,3,6-PhO(Ph) |
| 1.40 | CH$_3$ | 2,4,6-PhO(Ph) |
| 1.41 | CH$_3$ | 2,6-CF$_3$(Ph) |
| 1.42 | CH$_3$ | 2,3,6-CF$_3$(Ph) |
| 1.43 | CH$_3$ | 2,4,6-CF$_3$(Ph) |
| 1.44 | CH$_3$ | 2,6-CF$_3$O(Ph) |
| 1.45 | CH$_3$ | 2,3,6-CF$_3$O(Ph) |
| 1.46 | CH$_3$ | 2,4,6-CF$_3$O(Ph) |
| 1.47 | CH$_3$ | 2,3,4,6-Cl(Ph) |
| 1.48 | CH$_3$ | 2,3,5,6-Cl(Ph) |
| 1.49 | CH$_3$ | 2,3,4,5,6-Cl(Ph) |
| 1.50 | CH$_3$ | 2,3,4,6-Ph(Ph) |
| 1.51 | CH$_3$ | 2,3,5,6-Ph(Ph) |
| 1.52 | CH$_3$ | 2,3,4,5,6-Ph(Ph) |
| 1.53 | CH$_3$ | 2,3,4,6-PhO(Ph) |
| 1.54 | CH$_3$ | 2,3,5,6-PhO(Ph) |
| 1.55 | CH$_3$ | 2,3,4,5,6-PhO(Ph) |
| 1.56 | CH$_3$ | 2,3,4,6-Br(Ph) |
| 1.57 | CH$_3$ | 2,3,5,6-Br(Ph) |
| 1.58 | CH$_3$ | 2,3,4,5,6-Br(Ph) |
| 1.59 | CH$_3$ | 2,3,4,6-F(Ph) |
| 1.60 | CH$_3$ | 2,3,5,6-F(Ph) |
| 1.61 | CH$_3$ | 2,3,4,5,6-F(Ph) |
| 1.62 | CH$_3$ | 2,3,4,6-CH$_3$(Ph) |
| 1.63 | CH$_3$ | 2,3,5,6-CH$_3$(Ph) |
| 1.64 | CH$_3$ | 2,3,4,5,6-CH$_3$(Ph) |
| 1.65 | CH$_3$ | 2,3,4,6-C$_2$H$_5$(Ph) |
| 1.66 | CH$_3$ | 2,3,5,6-C$_2$H$_5$(Ph) |
| 1.67 | CH$_3$ | 2,3,4,5,6-C$_2$H$_5$(Ph) |
| 1.68 | CH$_3$ | 2,3,4,6-CH$_3$O(Ph) |
| 1.69 | CH$_3$ | 2,3,5,6-CH$_3$O(Ph) |
| 1.70 | CH$_3$ | 2,3,4,5,6-CH$_3$O(Ph) |
| 1.71 | CH$_3$ | 2,3,4,6-CF$_3$(Ph) |
| 1.72 | CH$_3$ | 2,3,5,6-CF$_3$(Ph) |
| 1.73 | CH$_3$ | 2,3,4,5,6-CF$_3$(Ph) |
| 1.74 | CH$_3$ | 2,3,4,6-CF$_3$O(Ph) |
| 1.75 | CH$_3$ | 2,3,5,6-CF$_3$O(Ph) |
| 1.76 | CH$_3$ | 2,3,4,5,6-CF$_3$O(Ph) |
| 1.77 | CH$_3$ | 2,3,4,6-CN(Ph) |
| 1.78 | CH$_3$ | 2,3,5,6-CN(Ph) |
| 1.79 | CH$_3$ | 2,3,4,5,6-CN(Ph) |
| 1.80 | CH$_3$ | 2-Br-6-Cl(Ph) |
| 1.81 | CH$_3$ | 2-Br-6-F(Ph) |
| 1.82 | CH$_3$ | 2-Br-6-CH$_3$(Ph) |
| 1.83 | CH$_3$ | 2-Br-6-CF$_3$(Ph) |
| 1.84 | CH$_3$ | 2-Br-6-CH$_3$O(Ph) |
| 1.85 | CH$_3$ | 2-Br-6-CF$_3$O(Ph) |
| 1.86 | CH$_3$ | 2-Br-6-CN(Ph) |
| 1.87 | CH$_3$ | 2-Cl-6-F(Ph) |
| 1.88 | CH$_3$ | 2-Cl-6-CH$_3$(Ph) |
| 1.89 | CH$_3$ | 2-Cl-6-CF$_3$(Ph) |
| 1.90 | CH$_3$ | 2-Cl-6-CH$_3$O(Ph) |
| 1.91 | CH$_3$ | 2-Cl-6-CF$_3$O(Ph) |

TABLE 1-continued

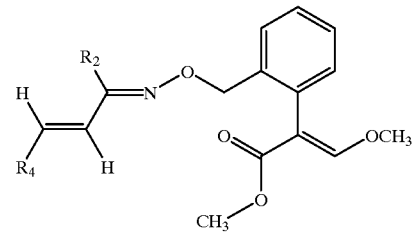

Formula IV'

| Compd # | R$_2$ | R$_4$ |
|---|---|---|
| 1.92 | CH$_3$ | 2-Cl-6-CN(Ph) |
| 1.93 | CH$_3$ | 2-F-6-CH$_3$(Ph) |
| 1.94 | CH$_3$ | 2-F-6-CF$_3$(Ph) |
| 1.95 | CH$_3$ | 2-F-6-CH$_3$O(Ph) |
| 1.96 | CH$_3$ | 2-F-6-CF$_3$O(Ph) |
| 1.97 | CH$_3$ | 6-CN,2-F(Ph) |
| 1.98 | CH$_3$ | 2-CH$_3$-6-CF$_3$(Ph) |
| 1.99 | CH$_3$ | 6-CH$_3$O-2-CH$_3$(Ph) |
| 1.100 | CH$_3$ | 2-CH$_3$-6-CF$_3$O(Ph) |
| 1.101 | CH$_3$ | 6-CN-2OMe(Ph) |
| 1.102 | CH$_3$ | 6-CN-2-CH$_3$(Ph) |
| 1.103 | CH$_3$ | 3,6-Cl-2-F(Ph) |
| 1.104 | CH$_3$ | 3-Cl-2,6-F(Ph) |
| 1.105 | CH$_3$ | 4-Cl-2,6-F(Ph) |
| 1.106 | CH$_3$ | 2-Br-3,6-Cl(Ph) |
| 1.107 | CH$_3$ | 6-Cl-2,3-Br(Ph) |
| 1.108 | CH$_3$ | 3-Cl-2,6-Br(Ph) |
| 1.109 | CH$_3$ | 2,6-Cl-3-F(Ph) |
| 1.110 | CH$_3$ | 2,3-Cl-6-F(Ph) |
| 1.111 | CH$_3$ | 2-Cl-3,6-F(Ph) |
| 1.112 | CH$_3$ | 3-Br-2,6-Cl(Ph) |
| 1.113 | CH$_3$ | 3-Br-2,6-F(Ph) |
| 1.114 | CH$_3$ | 3-Br-6Cl-2-F(Ph) |
| 1.115 | CH$_3$ | 2-Br-5Cl-6-F(Ph) |
| 1.116 | CH$_3$ | 2,6-Br-3-F(Ph) |
| 1.117 | CH$_3$ | 2,5-Br-6-F(Ph) |
| 1.118 | CH$_3$ | 2,4-Cl-6F(Ph) |
| 1.119 | CH$_3$ | 2,6-Cl-4F(Ph) |
| 1.120 | CH$_3$ | 6-Br-2,4-Cl(Ph) |
| 1.121 | CH$_3$ | 4-Br-2,6-Cl(Ph) |
| 1.122 | CH$_3$ | 6-Cl-2,4-F(Ph) |
| 1.123 | CH$_3$ | 6-Br-2,4-F(Ph) |
| 1.124 | CH$_3$ | 4-Br-2,6-F(Ph) |
| 1.125 | CH$_3$ | 2,4-Br-6-F(Ph) |
| 1.126 | CH$_3$ | 6-Cl-2,4-Br(Ph) |
| 1.127 | CH$_3$ | 4-Cl-2,6-Br(Ph) |
| 1.128 | CH$_3$ | 2,6-Br-4-F(Ph) |
| 1.129 | CH$_3$ | 2,4-Cl-6-CH$_3$(Ph) |
| 1.130 | CH$_3$ | 2,6-Cl-4-CH$_3$(Ph) |
| 1.131 | CH$_3$ | 2-Cl-4,6-(CH$_3$)$_2$(Ph) |
| 1.132 | CH$_3$ | 4-Cl-2,6-(CH$_3$)$_2$(Ph) |
| 1.133 | CH$_3$ | 2,4-F-6-CH$_3$(Ph) |
| 1.134 | CH$_3$ | 2,6-F-4-CH$_3$(Ph) |
| 1.135 | CH$_3$ | 2-F-4,6-(CH$_3$)$_2$(Ph) |
| 1.136 | CH$_3$ | 4-F-2,6-(CH$_3$)$_2$(Ph) |
| 1.137 | CH$_3$ | 2,4-Br-6-CH$_3$(Ph) |
| 1.138 | CH$_3$ | 2,6-Br-4-CH$_3$(Ph) |
| 1.139 | CH$_3$ | 2-Br-4,6-(CH$_3$)$_2$(Ph) |
| 1.140 | CH$_3$ | 4-Br-2,6-(CH$_3$)$_2$(Ph) |
| 1.141 | CH$_3$ | 2,4-Cl-6-CF$_3$(Ph) |
| 1.142 | CH$_3$ | 2,6-Cl-4-CF$_3$(Ph) |
| 1.143 | CH$_3$ | 2-Cl-4,6-(CF$_3$)$_2$(Ph) |
| 1.144 | CH$_3$ | 4-Cl-2,6-(CF$_3$)$_2$(Ph) |
| 1.145 | CH$_3$ | 2,4-F-6-CF$_3$(Ph) |
| 1.146 | CH$_3$ | 2,6-F-4-CF$_3$(Ph) |
| 1.147 | CH$_3$ | 2-F-4,6-(CF$_3$)$_2$(Ph) |
| 1.148 | CH$_3$ | 4-F-2,6-(CF$_3$)$_2$(Ph) |
| 1.149 | CH$_3$ | 2,4-Br-6-CF$_3$(Ph) |
| 1.150 | CH$_3$ | 2,6-Br-4-CF$_3$(Ph) |
| 1.137 | CH$_3$ | 2-Br-4,6-(CF$_3$)$_2$(Ph) |
| 1.138 | CH$_3$ | 4-Br-2,6-(CF$_3$)$_2$(Ph) |
| 1.139 | CH$_3$ | 2,4-Cl-6-CF$_3$O(Ph) |
| 1.140 | CH$_3$ | 2,6-Cl-4-CF$_3$O(Ph) |
| 1.141 | CH$_3$ | 2-Cl-4,6-(CF$_3$O)$_2$(Ph) |

TABLE 1-continued

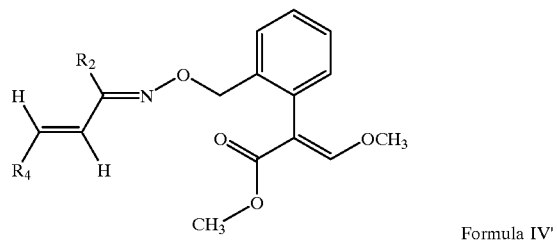

Formula IV'

| Compd # | R₂ | R₄ |
|---|---|---|
| 1.142 | CH₃ | 4-Cl-2,6-(CF₃O)₂(Ph) |
| 1.143 | CH₃ | 2,4-F-6-CF₃O(Ph) |
| 1.144 | CH₃ | 2,6-F-4-CF₃O(Ph) |
| 1.145 | CH₃ | 2-F-4,6-(CF₃O)₂(Ph) |
| 1.146 | CH₃ | 4-F-2,6-(CF₃O)₂(Ph) |
| 1.147 | CH₃ | 2,3-F-6-CF₃O(Ph) |
| 1.148 | CH₃ | 2,6-F-3-CF₃O(Ph) |
| 1.149 | CH₃ | 2-F-3,6-(CF₃O)₂(Ph) |
| 1.150 | CH₃ | 3-F-2,6-(CF₃O)₂(Ph) |
| 1.151 | CH₃ | 2-Br-3,4,6-Cl(Ph) |
| 1.152 | CH₃ | 6-F-2,4,5-Cl(Ph) |
| 1.153 | CH₃ | 6-Cl-2,4,5-Br(Ph) |
| 1.154 | CH₃ | 6-F-2,4,5-Br(Ph) |
| 1.155 | CH₃ | 2-Br-3,4,6-F(Ph) |
| 1.156 | CH₃ | 2-Cl-3,4,6-F(Ph) |
| 1.157 | CH₃ | 6-CH₃-2,4,5-Cl(Ph) |
| 1.158 | CH₃ | 6-CH₃-2,4,5-Br(Ph) |
| 1.159 | CH₃ | 6-CH₃-2,4,5-F(Ph) |
| 1.160 | CH₃ | 6-CF₃-2,4,5-Cl(Ph) |
| 1.161 | CH₃ | 2,4,5-Br-6-CF₃(Ph) |
| 1.162 | CH₃ | 2,4,5-F-6-CF₃(Ph) |
| 1.163 | CH₃ | 2,4,5-Cl-6-CF₃O(Ph) |
| 1.164 | CH₃ | 2,4,5-Br-6-CF₃O (Ph) |
| 1.165 | CH₃ | 2,4,5-F-6-CF₃O(Ph) |
| 1.166 | CH₃ | 2-Br-3,5,6-Cl(Ph) |
| 1.167 | CH₃ | 2-Br-3,5,6-F(Ph) |
| 1.168 | CH₃ | 2-Cl-3,5,6-F(Ph) |
| 1.169 | CH₃ | 6-F-2,3,5-Cl(Ph) |
| 1.170 | CH₃ | 6-Cl-2,3,5-Br(Ph) |
| 1.171 | CH₃ | 6-F-2,3,5-Br(Ph) |
| 1.172 | CH₃ | 6-CH₃-2,3,5-Cl(Ph) |
| 1.173 | CH₃ | 6-CH₃-2,3,5-Br(Ph) |
| 1.174 | CH₃ | 2-CH₃-3,5,6-F(Ph) |
| 1.175 | CH₃ | 2,3,5-Cl-6-CF₃(Ph) |
| 1.176 | CH₃ | 2,3,5-Br-6-CF₃(Ph) |
| 1.177 | CH₃ | 3,5,6-F-2-CF₃(Ph) |
| 1.178 | CH₃ | 2,3,5-Cl-6-CF₃O(Ph) |
| 1.179 | CH₃ | 2,3,5-Br-6-CF₃O(Ph) |
| 1.180 | CH₃ | 3,5,6-F-2-CF₃O(Ph) |
| 1.172 | CH₃ | 4-Br-2,3,5,6-Cl(Ph) |
| 1.173 | CH₃ | 4-F-2,3,5,6-Cl(Ph) |
| 1.174 | CH₃ | 4-Cl-2,3,5,6-Br(Ph) |
| 1.175 | CH₃ | 4-F-2,3,5,6-Br(Ph) |
| 1.176 | CH₃ | 4-Cl-2,3,5,6-F(Ph) |
| 1.177 | CH₃ | 4-Br-2,3,5,6-F(Ph) |
| 1.178 | CH₃ | 2-Br-3,4,5,6-Cl(Ph) |
| 1.179 | CH₃ | 2-F-3,4,5,6-Cl(Ph) |
| 1.180 | CH₃ | 2-Cl-3,4,5,6-F(Ph) |
| 1.181 | CH₃ | 2-Br-3,4,5,6-F(Ph) |
| 1.182 | CH₃ | 6-Cl-2,3,4,5-Br(Ph) |
| 1.183 | CH₃ | 6-F-2,3,4,5-Br(Ph) |
| 1.184 | CH₃ | 4-CH₃-2,3,5,6-Cl(Ph) |
| 1.185 | CH₃ | 4-CH₃-2,3,5,6-Br(Ph) |
| 1.186 | CH₃ | 4-CH₃-2,3,5,6-F(Ph) |
| 1.187 | CH₃ | 4-CF₃-2,3,5,6-Cl(Ph) |
| 1.188 | CH₃ | 4-CF₃-2,3,5,6-Br(Ph) |
| 1.189 | CH₃ | 4-CF₃-2,3,5,6-F(Ph) |
| 1.190 | CH₃ | 4-CH₃O-2,3,5,6-Cl(Ph) |
| 1.191 | CH₃ | 2,3,5,6-Br-4-CF₃O(Ph) |
| 1.192 | CH₃ | 2,3,5,6-F-4-CF₃O(Ph) |
| 1.193 | CH₃ | 2,3,5,6-Cl-4-CF₃O(Ph) |
| 1.194 | CH₃ | 6-CH₃-2,3,4,5-Cl(Ph) |
| 1.195 | CH₃ | 6-CH₃-2,3,4,5-BrPh) |
| 1.196 | CH₃ | 3,4,5,6-F-2-CH₃(Ph) |
| 1.197 | CH₃ | 2,3,4,5-Cl-6-CF₃O(Ph) |
| 1.198 | CH₃ | 2,3,4,5-Br-6-CF₃O(Ph) |
| 1.199 | CH₃ | 2-CF₃O-3,4,5,6-F(Ph) |
| 1.200 | C₂H₅ | 2,6-Cl(Ph) |
| 1.201 | C₂H₅ | 2,3,6-Cl(Ph) |
| 1.202 | C₂H₅ | 2,4,6-Cl(Ph) |
| 1.203 | C₂H₅ | 2,6-Br(Ph) |
| 1.204 | C₂H₅ | 2,3,6-Br(Ph) |
| 1.205 | C₂H₅ | 2,4,6-Br(Ph) |
| 1.206 | C₂H₅ | 2,6-F(Ph) |
| 1.207 | C₂H₅ | 2,3,6-F(Ph) |
| 1.208 | C₂H₅ | 2,4,6-F(Ph) |
| 1.209 | C₂H₅ | 2,6-CH₃(Ph) |
| 1.210 | C₂H₅ | 2,3,6-CH₃(Ph) |
| 1.211 | C₂H₅ | 2,4,6-CH₃(Ph) |
| 1.212 | cyclopropyl | 2,6-Cl(Ph) |
| 1.213 | cyclopropyl | 2,3,6-Cl(Ph) |
| 1.214 | cyclopropyl | 2,4,6-Cl(Ph) |
| 1.215 | cyclopropyl | 2,6-F(Ph) |
| 1.216 | cyclopropyl | 2,3,6-F(Ph) |
| 1.217 | cyclopropyl | 2,4,6-F(Ph) |
| 1.218 | CH₂=CH | 2,6-Cl(Ph) |
| 1.219 | CH₂=CH | 2,3,6-Cl(Ph) |
| 1.220 | CH₂=CH | 2,4,6-Cl(Ph) |
| 1.221 | n-C₃H₇ | 2,6-Cl(Ph) |
| 1.222 | n-C₃H₇ | 2,3,6-Cl(Ph) |
| 1.223 | n-C₃H₇ | 2,4,6-Cl(Ph) |
| 1.224 | CN | 2,6-Cl(Ph) |
| 1.225 | CN | 2,4,6-Cl(Ph) |
| 1.226 | CF₃ | 2,6-Cl(Ph) |
| 1.227 | CF₃ | 2,3,6-Cl(Ph) |

Compounds 2.1 to 2.227 are compounds of Formula I, wherein Y is O; X is N; and A, R₃, and R₅ are hydrogen which are compounds of Formula V' wherein R₂ and R₄ are as defined in Table 1 for compounds 1.1 to 1.227.

Compounds 3.1 to 3.227 are compounds of Formula I, wherein Y is NH; X is N; R₁ is methyl; and A, R₃, and R₅ are hydrogen which are compounds of Formula VII' wherein R₂ and R₄ are as defined in Table 1 for compounds 1.1 to 1.227.

Typical compounds of Formula I encompassed by the present invention wherein Y is O are compounds of Formula IV wherein A, R₃, and R₅ are hydrogen; and X is CH including those compounds of Formula IV' presented in Table 4 wherein R₂ and R₄ are as defined in Table 4

TABLE 4

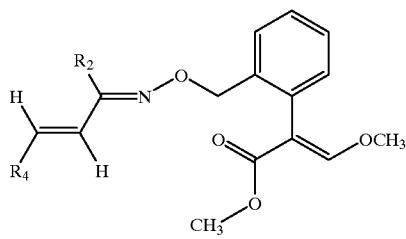

Formula IV'

| Compd # | R$_2$ | R$_4$ |
|---|---|---|
| 4.1 | H | 2,4-Cl-pyrid-3-yl |
| 4.2 | H | 2,4-F-pyrid-3-yl |
| 4.3 | H | 2-Cl-4-F-pyrid-3-yl |
| 4.4 | H | 2,4-(CH$_3$)$_2$-pyrid-3-yl |
| 4.5 | H | 3,5-Cl-pyrid-4-yl |
| 4.6 | H | 3,5-F-pyrid-4-yl |
| 4.7 | H | 3-Cl-5-F-pyrid-4-yl |
| 4.8 | H | 3,5-(CH$_3$)$_2$-pyrid-4-yl |
| 4.9 | H | 4,6-Cl-pyrimidin-5-yl |
| 4.10 | H | 4,6-F-pyrimidin-5-yl |
| 4.11 | H | 4,6-(CH$_3$)$_2$-pyrimidin-5-yl |
| 4.12 | H | 4-Cl-6-F-pyrimidin-5-yl |
| 4.13 | CH$_3$ | 2,4-Cl-pyrid-3-yl |
| 4.14 | CH$_3$ | 2,4-F-pyrid-3-yl |
| 4.15 | CH$_3$ | 2-Cl-4-F-pyrid-3-yl |
| 4.16 | CH$_3$ | 2,4-(CH$_3$)$_2$-pyrid-3-yl |
| 4.17 | CH$_3$ | 3,5-Cl-pyrid-4-yl |
| 4.18 | CH$_3$ | 3,5-F-pyrid-4-yl |
| 4.19 | CH$_3$ | 3-Cl-5-F-pyrid-4-yl |
| 4.20 | CH$_3$ | 3,5-(CH$_3$)$_2$-pyrid-4-yl |
| 4.21 | CH$_3$ | 4,6-Cl-pyrimidin-5-yl |
| 4.22 | CH$_3$ | 4,6-F-pyrimidin-5-yl |
| 4.23 | CH$_3$ | 4,6-(CH$_3$)$_2$-pyrimidin-5-yl |
| 4.24 | CH$_3$ | 4-Cl-6-F-pyrimidin-5-yl |
| 4.25 | CH$_3$ | 3,5-Cl-pyridazin-4-yl |
| 4.26 | CH$_3$ | 3,5-F-pyridazin-4-yl |
| 4.27 | CH$_3$ | 3,5-Br-pyridazin-4-yl |
| 4.28 | CH$_3$ | 3,5-(CH$_3$)$_2$-pyridazin-4-yl |
| 4.29 | CH$_3$ | 3-Cl-5-F-pyridazin-4-yl |
| 4.30 | CH$_3$ | 5-Cl-3-F-pyridazin-4-yl |
| 4.31 | CH$_3$ | 3-Br-5-Cl-pyridazin-4-yl |
| 4.32 | CH$_3$ | 5-Br-3-Cl-pyridazin-4-yl |
| 4.33 | CH$_3$ | 2,4-Cl-thien-3-yl |
| 4.34 | CH$_3$ | 2,4-F-thien-3-yl |
| 4.35 | CH$_3$ | 2-Cl-4-F-thien-3-yl |
| 4.36 | CH$_3$ | 2-F-4-Cl-thien-3-yl |
| 4.37 | CH$_3$ | 2,4-(CH$_3$)$_2$-thien-3-yl |
| 4.38 | CH$_3$ | 2,4,5-Cl-thien-3-yl |
| 4.39 | CH$_3$ | 2,4,5-F-thien-3-yl |
| 4.40 | CH$_3$ | 2,4,5-CH$_3$-thien-3-yl |
| 4.41 | CH$_3$ | 2,4-Cl-furan-3-yl |
| 4.42 | CH$_3$ | 2,4-F-furan-3-yl |
| 4.43 | CH$_3$ | 2-Cl-4F-furan-3-yl |
| 4.44 | CH$_3$ | 2-F-4Cl-furan 3-yl |
| 4.45 | CH$_3$ | 2,4-(CH$_3$)$_2$-furan -3-yl |
| 4.46 | CH$_3$ | 2,4,5-Cl-furan-3-yl |
| 4.47 | CH$_3$ | 2,4,5-F-furan-3-yl |
| 4.48 | CH$_3$ | 2,4,5-CH$_3$-furan-3-yl |
| 4.49 | CH$_3$ | 2,4-Cl-1-CH$_3$-1H-pyrrol-3-yl |
| 4.50 | CH$_3$ | 2,4-F-1-CH$_3$-1H-pyrrol-3-yl |
| 4.51 | CH$_3$ | 2-Cl-4F-1-CH$_3$-1H-pyrrol-3-yl |
| 4.52 | CH$_3$ | 2-F-4Cl-1-CH$_3$-1H-pyrrol-3-yl |
| 4.53 | CH$_3$ | 3,5-Cl-isoxazol-4-yl |
| 4.54 | CH$_3$ | 3,5-F-isoxazol-4-yl |
| 4.55 | CH$_3$ | 3,5-Br-isoxazol-4-yl |
| 4.56 | CH$_3$ | 3,5-CH$_3$-isoxazol-4-yl |
| 4.57 | CH$_3$ | 3,5-CH$_3$O-isoxazol-4-yl |
| 4.58 | CH$_3$ | 3,5-CF$_3$O-isoxazol-4-yl |
| 4.50 | CH$_3$ | 3,5-Cl-isothiazol-4-yl |
| 4.60 | CH$_3$ | 3,5-F-isothiazol-4-yl |
| 4.61 | CH$_3$ | 3,5-Br-isothiazol-4-yl |
| 4.62 | CH$_3$ | 3,5-CH$_3$-isothiazol-4-yl |
| 4.63 | CH$_3$ | 3,5-CH$_3$O-isothiazol-4-yl |
| 4.64 | CH$_3$ | 3,5-CF$_3$O-isothiazol-4-yl |

TABLE 4-continued

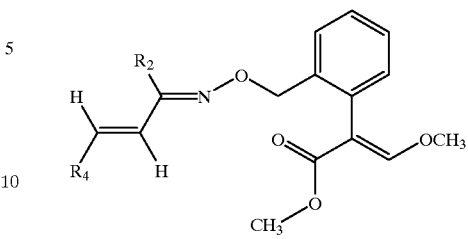

Formula IV'

| Compd # | R$_2$ | R$_4$ |
|---|---|---|
| 4.66 | CH$_3$ | 3,5-Cl-1-CH$_3$-1H-pyrazol-4-yl |
| 4.67 | CH$_3$ | 3,5-F-1-CH$_3$-1H-pyrazol-4-yl |
| 4.68 | CH$_3$ | 3,5-Br-1-CH$_3$-1H-pyrazol-4-yl |
| 4.69 | CH$_3$ | 3-Cl-5F-1-CH$_3$-1H-pyrazl-4-yl |
| 4.70 | CH$_3$ | 2,4-Cl-pyrid-3-yl |
| 4.71 | CH$_3$ | 2,4-F-pyrid-3-yl |
| 4.72 | CH$_3$ | 2-Cl-4-F-pyrid-3-yl |
| 4.73 | CH$_3$ | 2,4-(CH$_3$)$_2$-pyrid-3-yl |
| 4.74 | CH$_3$ | 3,5-Cl-pyrid-4-yl |
| 4.75 | CH$_3$ | 3,5-F-pyrid-4-yl |
| 4.76 | CH$_3$ | 3-Cl-5-F-pyrid-4-yl |
| 4.77 | CN | 2,4-Cl-pyrid-3-yl |
| 4.78 | CN | 2,4-F-pyrid-3-yl |
| 4.79 | CN | 2-Cl-4-F-pyrid-3-yl |
| 4.80 | CN | 2,4-(CH$_3$)$_2$-pyrid-3-yl |
| 4.81 | CN | 3,5-Cl-pyrid-4-yl |
| 4.82 | CN | 3,5-F-pyrid-4-yl |
| 4.83 | CN | 3-Cl-5-F-pyrid-4-yl |
| 4.84 | CN | 4,6-Cl-pyrimidin-5-yl |
| 4.85 | CN | 4,6-F-pyrimidin-5-yl |
| 4.86 | CN | 2,4-Cl-thien-3-yl |
| 4.87 | CN | 2,4-F-thien-3-yl |
| 4.88 | CN | 2-Cl-4-F-thien-3-yl |
| 4.89 | CN | 2-F-4-Cl-thien-3-yl |
| 4.90 | CN | 2,4-(CH$_3$)$_2$-thien-3-yl |
| 4.89 | CN | 2,4,5-Cl-thien-3-yl |
| 4.90 | CN | 2,4,5-F-thien-3-yl |
| 4.91 | CN | 2,4,5-CH$_3$-thien-3-yl |
| 4.92 | CN | 2,4-Cl-pyrid-3-yl |
| 4.93 | CN | 2,4-Cl-pyrid-3-yl |
| 4.94 | CN | 2,4-Cl-thien-3-yl |
| 4.95 | CN | 2,4-F-thien-3-yl |
| 4.96 | CN | 2-Cl-4-F-thien-3-yl |
| 4.97 | CN | 2-F-4-Cl-thien-3-yl |
| 4.98 | CN | 2,4-(CH$_3$)$_2$-thien-3-yl |
| 4.99 | CF$_3$ | 2,4-Cl-pyrid-3-yl |
| 4.100 | CF$_3$ | 2,4-F-pyrid-3-yl |
| 4.101 | CF$_3$ | 2,4-Cl-thien-3-yl |
| 4.102 | CF$_3$ | 2,4-F-thien-3-yl |
| 4.103 | CF$_3$ | 2-Cl-4-F-thien-3-yl |
| 4.104 | CF$_3$ | 2-F-4-Cl-thien-3-yl |
| 4.105 | CF$_3$ | 2,4-(CH$_3$)$_2$-thien-3-yl |
| 4.106 | CF$_3$ | 3,5-Cl-isothiazol-4-yl |
| 4.107 | CF$_3$ | 3,5-F-isothiazol-4-yl |
| 4.108 | cyclopropyl | 2,4-Cl-pyrid-3-yl |
| 4.109 | cyclopropyl | 2,4-F-pyrid-3-yl |
| 4.110 | cyclopropyl | 2,4-Cl-thien-3-yl |
| 4.111 | cyclopropyl | 2,4-F-thien-3-yl |

Compounds 5.1 to 5.111 are compounds of Formula I, wherein Y is O ; X is N; and A, R$_3$, and R$_5$ are hydrogen which are compounds of Formula V wherein R$_2$ and R$_4$ are as defined in Table 4 for compounds 4.1 to 4.111.

Compounds 6.1 to 6.111 are compounds of Formula I, wherein Y is NH, X is N; R$_1$ is methyl; and A, R$_3$, and R$_5$ are hydrogen which are compounds of Formula VII' wherein R$_2$ and R$_4$ are as defined in Table 4 for compounds 4.1 to 4.111.

As used in Tables 1 to 6 Ph is understood to be phenyl.

Scheme A describes the preparation of compounds of the Formula (I). where X is CH or N, and Y is O (compounds of formula IV and V). The unsaturated oximes (III) are reacted with the appropriately substituted benzyl derivatives (II) where Z is a halogen, such as bromo, chloro or iodo, preferably a benzyl bromide. An unsaturated oxime represented by the general formula (III) is treated, at room temperature, with an appropriate base to form an anion, followed by the addition of a benzyl bromide (II). Typical bases employed are metal hydrides such as sodium hydride, alkoxides such as sodium methoxide and hydroxide bases such as sodium or potassium hydroxide and alkali bases such as sodium or potassium carbonate. Typical solvents employed with hydride bases are N,N-dimethylformamide (DMF) and tetrahydrofuran (THF); with hydroxide bases DMF, THF, methyl ethyl ketone (MEK) and acetone and with alkali bases solvents such as DMF, acetone, and MEK.

As shown in Scheme A, the oxime appears in the E position (assuming $R_3C=CR_4R_5$ is the larger substituent). It should be recognized that the Z isomer can also be produced, as well as isomeric mixtures. When isomers are produced they are designated isomer A (higher $R_f$ on thin layer chromatography) and isomer B (lower $R_f$ on thin layer chromatography). The determination of which isomer, A or B possesses the E or Z geometry can be made by such conventional techniques as X ray crystallography or by spectroscopic means such as nuclear magnetic resonance spectroscopy. For the compounds of the present invention isomer A has been assigned the E iminoxy configuration and isomer B, the Z iminoxy configuration.

Scheme A

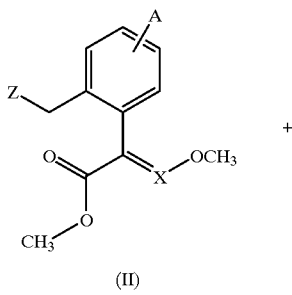

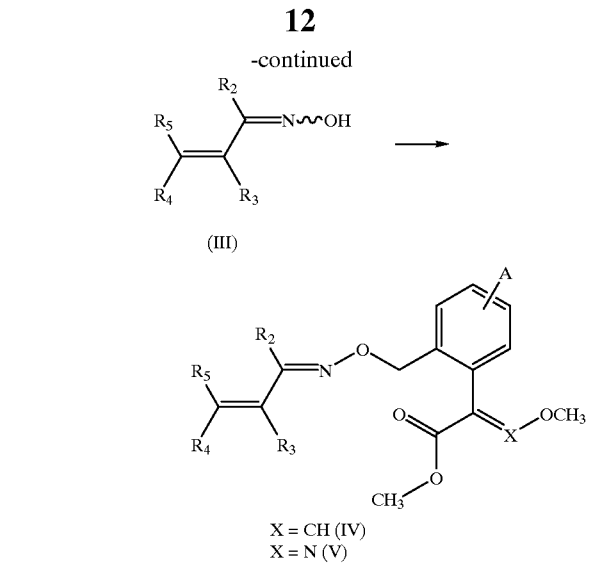

Compounds of formula IV (X is CH) are prepared in an analogous manner by alkylation with methyl E-α-(2-bromomethylphenyl)-β-methoxyacrylate in the presence of a base, preferably NaOH or KOH, in a solvent, preferably acetone or methyl ethyl ketone. Methyl E-α-(2-bromomethylphenyl)-β-methoxyacrylate, as a single E isomer, can be prepared in two steps from 2-methylphenylacetate as described previously in U.S. Pat. No. 4,914,128. Compounds of formula V (X=N) are prepared by the reaction with methyl E-2-(bromomethyl)-phenyl-glyoxylate O-methyloxime in the presence of a base, preferably NaOH or KOH, in a solvent, preferably acetone or methyl ethyl ketone. Methyl 2-(bromomethyl)-phenylglyoxylate O-methyloxime can be prepared as described in U.S. Pat. Nos. 4,999,042 and 5,157,144. Methyl 2-(bromomethyl)-phenylglyoxylate O-methyl-oxime is prepared from methyl 2-methylphenyl-acetate by treatment with an alkyl nitrite under basic conditions to provide after methylation, methyl 2-methyl-phenyl-glyoxalate O-methyl oxime which can also be prepared from methyl 2-methyl-phenylglyoxalate by treatment with 2-hydroxylamine hydrochloride and methylation or by treatment with methoxylamine hydrochloride.

Scheme B

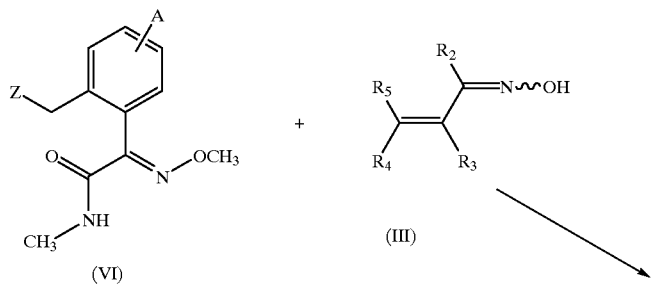

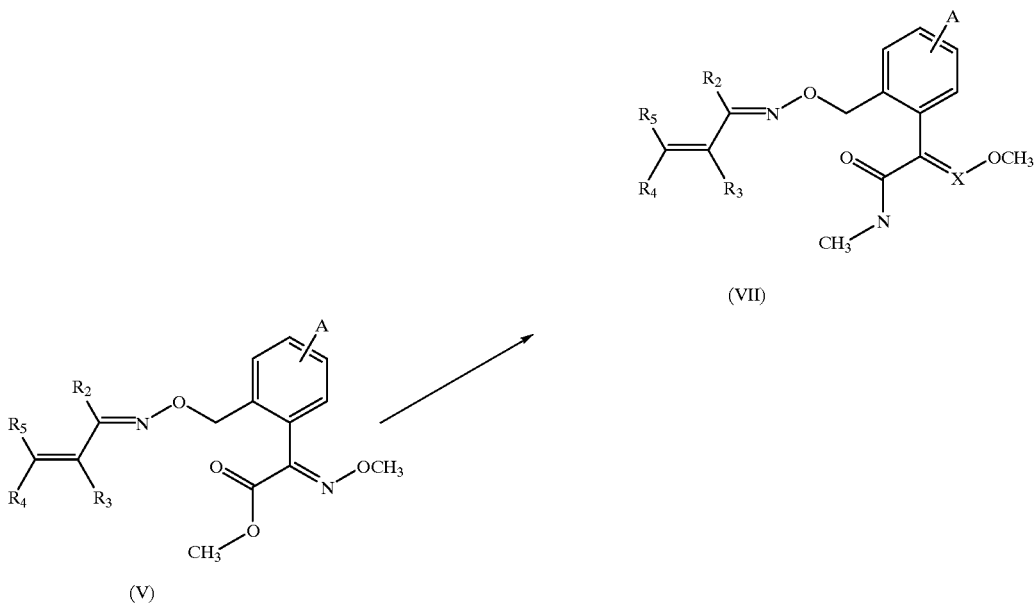

(VII)

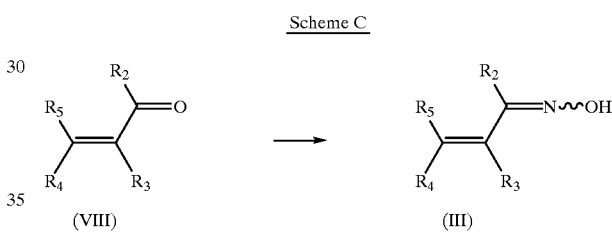

(V)

As shown in scheme B. compounds of formula VII (X is N) can be prepared by the aminolysis of oximinoacetate (V). The aminolysis of oximinoacetate to oximinoacetamides has been described in U.S. Pat. Nos. 5,185,342, 5,221,691, 5,407,902. For example, compounds of Table II of formula V' where X is N and Y is O are treated with 40% aqueous methylamine in methanol to provide compounds of Table III of formula VII' where Y is NH. Alternatively, as is shown in scheme B intermediate unsaturated oximes (III) are reacted with N-Methyl (E)-2-methoxyimino-2-[2-(bromomethyl)-phenyl]-acetamide in the presence of a base such as an hydroxide base preferably in a solvent such as acetone or methyl ethyl ketone to provide compounds of Table II of formula (V'). N-Methyl (E)-2-methoxy-imino-2-[2-(bromomethyl)-phenyl]acetamide is described in U.S. Pat. No. 5,387,714.

The oximes of the general formula (III) can be obtained, as shown in scheme C, by reacting the corresponding α,β-unsaturated aldehyde or ketone (VIII) with hydroxylamine hydrochloride from room temperature to reflux, preferably at room temperature, in an appropriate solvent such as methanol or ethanol in the presence of an appropriate alkali such as sodium hydroxide or potassium carbonate. A general description of the synthesis of oximes with hydroxyl amine is described in March, *Advanced Organic Chemistry*, 4th Ed, pp. 906–907 and references therein. The oximes of the general formula (III) when obtained as a mixture of syn or anti oxime isomers can be separated into individual isomers and alkylated as described in Schemes A and B. When a mixture of oximes of the general formula (III) are used in Schemes A and B the compounds of the formula IV, V and VII can be separated into their individual isomers by conventional chromatographic techniques.

Scheme C

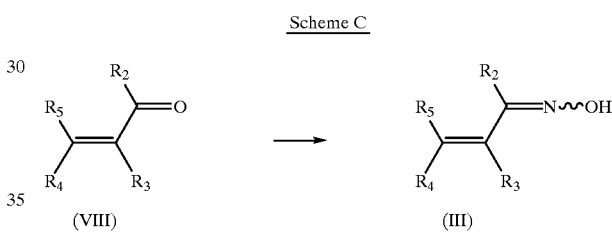

(VIII)                    (III)

The α,β-unsaturated aldehydes or ketones (VIII) can be prepared by conventional condensation techniques. A extensive description of the synthesis of α,β-unsaturated aldehydes or ketones (enones) is described in March, *Advanced Organic Chemistry*, 4th Ed, pp. 937–955 and references therein. For example *Organic Reactions*, Volume 16 describes the general aldol condensation of ketones and aldehydes. For compounds of formula I of this invention, in general the ketones or aldehydes can be $R_4COR_5$ where $R_4$ and $R_5$ are defined previously or the ketones and aldehydes can be $R_2COCH_2R_3$ where $R_2$ and $R_3$ are defined as in formula I. Typically the ketone is dissolved in a hydroxylic solvent, such as methanol or ethanol, to which is added dropwise a solution of the aldehyde in an aqueous basic solution. The typical bases used can be alkali metal hydroxides, such as barium, potassium or sodium hydroxide and the dropwise addition is conducted from 0° C. to 35° C. preferably at ambient temperature. When the enone is derived from acetone ($R_2$ is methyl and $R_3$ is hydrogen) the solvent is preferably acetone to which is added $R_4COR_5$ followed by the aqueous hydroxide solution. The o,o'-disubstituted ketones or aldehydes of the present invention, $R_4COR_5$, are commercially available or can be prepared by conventional synthetic methods A direct synthesis of compounds of the formula V or VII is shown in Scheme H. Compounds of the Formula V or VII can be prepared directly from the functionalized unsaturated ketones or aldehydes, VIII, by condensation with the aminoxy intermediate IX. The preparation of aminoxy intermediate IX is described in U.S. Pat. No. 5,194,662. The aminoxy intermediate IX is prepared in a two step sequence by the alkylation of II (where X is N) with N-hydroxyphthalimide which is treated with hydrazine to provide IX. The aminoxy intermediate IX is condensed with ketones or aldehydes VIII to provide V which is treated as shown in scheme B to provide VII.

Scheme D

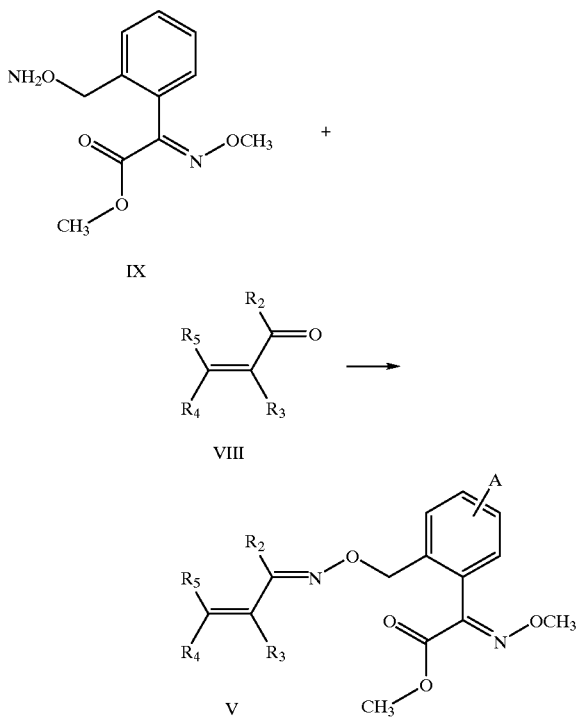

The following examples are illustrative of the present invention

EXAMPLES 1
Preparation of E and E/Z imine isomers: (E,E,E) and (E and Z,E,E) of Methyl 2-[2-((((1-methyl-3-(2',6'-difluoroiphenyl)-trans-2-propenyhlidene)amino)oxy)methyl)-phenyl]-2-methoxyiminoacetate(Compound 2.22A of Table 2).
Preparation of trans-4-(2,6-difluorophenyl)-3-buten-2-one
To a 100ml reaction bottle equipped with magnetic stir bar was charged 5.0 g (35.2 mmole) of 2,6-difluorobenzaldehyde in 20 ml acetone and to this was added 3.4 g of 50% aqueous NaOH (42 mmole) in 60 ml water (exothermic) and stirred at room temperature. The reaction was monitored by GLC and after 2 hours the reaction was worked up. The reaction mixture was extracted with 50 ml CHCl$_3$, washed with 50 ml H$_2$O, dried over anhydrous MgSO4, filtered, and the solvent removed in vacuuo on a rotary evaporator to afford 5.7 g of trans-4-(2,6-difluorophenyl)-3-buten-2-one as a yellow oil in 81% purity by GC. and 89.5% isolated yield.
NMR (300 MHz $^1$H CDCl$_3$): 2.4 (s, 3H); 6.9 (m, 3H); 7.3 (m, 1H); 7.6 (d, 1H).
Preparation of E,E,E isomer (isomer A): Methyl 2-[2-((((1-methyl-3-(2',6'-difluorolphenyl)-trans-2-propenylidene)amino)oxy)methyl)-phenyl]-2-methoxy-iminoacetate To a 100 ml round bottom flask equipped with magnetic stir bar was charged 0.60 g (3.3 mmole) of trans-2,6-difluorophenyl)-3-buten-2-one in 5 ml MeOH, 1.07 g (4.4 mmole) of methyl (E)-2-(aminooxymethyl)-phenyl glyoxylate O-methyloxime in 5 ml MeOH, and 0.5 ml acetic acid catalyst. The solution was stirred 4 hours at ambient temperature and then concentrated in vacuuo to give a wet solid. The wet solid was vacuum filtered and washed with hexane to give 190 mg isomer-A (99.5% isomer-A/0.5% isomer-B by GLC) of (E,E,E) methyl 2-[2-((((1-methyl-3-(2',6'-difluorophenyl)-trans-2-propenylidene)amino)oxy)methyl)-phenyl]-2-methoxy-iminoacetate as a white solid, mp 97–100° C. in a 14.4% isolated yield. The filtrate after solvent removal gave 1.4 g of a yellow which contained 59:41 A:B isomer ratio in 70% chemical purity.
NMR (300 MHz $^1$H CDCl$_3$): 2.05(s, 3H); 3.86(s, 3H); 4.04(s, 3H); 5.08(s, 2H); 6.8-7.5(m, 9H).

EXAMPLE 2
Preparation of E and Z imine isomers: (E,E,E) and (Z,E,E) of N-Methyl 2-[2-((((1-methyl-3-(2',6'-difluorophenyl)-trans-2-propenylidene)amino)oxy)methyl)-phenyl]-2-methoxyiminoacetamide (Compounds 3.22A and 3.22B of Table 3).
To a 25 ml reaction test tube under nitrogen atmosphere was charged 1.4 g (59:41 A:B isomer of 70% chemical purity) of (E,E,E) and (Z,E,E)-methyl 2-[2-((((1-methyl-3-(2',6'-difluorophenyl)-trans-2-propenylidene)amino)oxy) methyl)-phenyl]-2-methoxy-iminoacetate (3.5 mmole) in 10 ml MeOH and 1.3 g methyl amine (40% aqueous solution, 17 mmole) which was heated at reflux. The reaction was monitored by GLC and worked up after 1.5 hours. The methanol was removed in vacuuo on the rotary evaporator at 30° C. To the residue was added 125 ml ethyl acetate and 50 ml water, partitioned, and the organic phase further washed with 3×50 ml water, dried over anhydrous MgSO$_4$, and concentrated in vacuuo on the rotary evaporator to give 1.1 g crude product as a yellow oil in a 57:43 A:B isomer ratio which was chromatographed on silica with 2:3 ethyl acetate/hexane to afford both isomer A (E,E,E) and isomer B (Z,E,E) of N-methyl 2-[2-((((1-methyl-3-(2',6'-difluorophenyl)-trans-2-propenylidene)amino)oxy)methyl)-phenyl]-2-methoxyiminoacetamide after trituration with ether and hexane as solids. Chromatography afforded 210 mg of isomer-A (E,E,E) as a white solid, mp =79–82° C. and 230 mg of isomer-B (Z,E,E) as a white solid, mp =129–132° C. in an overall isolated yield of 44.9%.
NMR isomer-A (300 MHz $^1$H CDCl$_3$): 2.05(s, 3H); 2.91(d, 3H); 3.96(s, 3H);5.08(s, 2H); 6.7-7.5(m, 9H).
NMR isomer-B (300 MHz $^1$H CDCl$_3$): 2.07(s, 3H); 2.86(d, 3H); 3.92(s, 3H); 5.05(s,2H); 6.7-7.7(m, 9H).

EXAMPLE 3
Preparation of E/Z imine isomers: (E and Z,E,E) of Methyl 2-[2-((((1-methyl-3-(2'-chloro-6'-fluorophenyl)-trans-2-propenylidene)amino)oxy) methyl)-phenyl]-2-methoxyiminoacetate (Compound 2.87 of Table 2).
Preparation of trans-4-(2-fluoro,6-chlorohenyl)-3-buten-2-one
Using the method of Example 1 step 1: To 5.15 g (32.5 mmole) 2-fluoro-6-chloro benzaldehyde in 20 ml acetone was added 3.1 g 50% aqueous NaOH (39.0 mmole) in 100 ml water. After stirring for 4 hours 5.85 g of trans-4-(2-fluoro-6-chlorophenyl)-3-buten-2-one was isolated as a yellow oil in a 90.7% isolated yield (94.6% purity by GLC).
Preparation of E/Z imine isomers: (E and Z,E,E) of Methyl 2-[2-((((1-methyl-3-(2-'-chloro-6'-fluorophenyl)-trans-2-propenylidene)amino)methyl)-phenyl]-2-methoxyiminoacetate Using the method of Example 1 step 2: To 1.62 g (8.2 mmole) of trans-4-(2-fluoro,6-chlorophenyl)-3-buten-2-one in 5 ml MeOH, was added 2.72 g (11.4 mmole) methyl (E)-2-(aminooxymethyl)-phenyl glyoxylate O-methyloxime in 5 ml MeOH and 1 ml acetic acid catalyst. The mixture was stirred for 4 hours and worked up to give a wet solid which was washed with hexane. 2.1 g of methyl 2-[2-((((1-methyl-3-(2'-chloro-6'-fluorophenyl)-trans-2-propenylidene)amino)oxy)methyl)-phenyl]-2-methoxyiminoacetate was isolated (61.8% yield). as a white solid in a 70/30 A:B (E,E,E:Z,E,E) isomer ratio, mp. 110–116° C. NMR (300 MHz $^1$H CDCl$_3$): 2.07(d, 3H); 3.86(d, 3H); 4.02(d, 3H); 5.09(d, 2H); 7–7.6(m, 9H).

EXAMPLE 4

Preparation of E/Z imine isomers: (E and Z,E,E) of N-Methyl 2-[2-((((1-methyl-3-(2'-chloro-6'-fluorophenyl-trans-2-propenylidene)amino)oxy)methyl)-phenyl]-2-methoxyiminoacetamide (Compounds 3.87 of Table 3).

Using the method of Example 2, 1.3g (7:3 isomer A:B) of methyl 2-[2-((((1-methyl-3-(2'-chloro-6'-fluorophenyl)-trans-2-propenylidene)amino)oxy)methyl)-phenyl]-2-methoxyiminoacetate (3.1 mmole) in 20 ml MeOH, and 1.2 g (15.5 mmole) 40% aqueous methyl amine was heated for 2 hours at reflux; 0.6g (7.7 mmole) more methyl amine was added and the mixture was heated for an additional 30 min and worked up to give 1.1 g of a 70/30 A:B isomer mixture of (E and Z, E, E) N-methyl 2-[2-((((1-methyl-3-(2'-chloro-6'-fluorophenyl)-trans-2-propenylidene)amino)oxy)methyl)-phenyl]-2-methoxyiminoacetamide as a tacky off-white gum in a 85.3% isolated yield. NMR (300 MHz $^1$H CDCl$_3$): 2.08(d, 3H); 3.85(d, 3H); 4.04(d, 3H); 5.06(d, 2H); 6.7–7.6(m, 8H).

EXAMPLE 5

Preparation of E/Z imine isomers: (E and Z,E,E) of Methyl 2-[2-((((1-methyl-3-(2',3',6'-tri-chloroihenyl)-trans-2-propenylidene)amino)oxy)methyl)-phenyl]-2-methoxyiminoacetate(Compound 2.17 of Table 2).

Preparation of trans 4-(2,3,6-trichlorophenyl)-3-buten-2-one

Using the method of Example 1 step 1: To 5.0 g (23.9 mmole) of 2,3,6-trichloro benzaldehyde in 20 ml acetone, was added 2.3 g 50% aqueous NaOH (28.7 mmole) in 100 ml water; After 4 hours the reaction mixture was worked u to give 5.5 g of the trans-4-(2,3,6-trichlorophenyl)-3-buten-2-one as a yellow oil with solid in a 92.3% yield (99% purity by GLC).

Preparation of E/Z imine isomers: (E and Z,E,E) of Methyl 2-[2-((((1-methyl-3-(2',3',6'-tri-chlorophenyl)-trans-2-propenylidene)amino)oxy)methyl)phenyl]-2-methoxyiminoacetate Using the method of Example 1 step 2: To 0.80 g (3.2 mmole) trans-4-(2,3,6-trichlorophenyl)-3-buten-2-one in 5 ml MeOH, was added 1.03 g (11.4 mmole methyl (E)-2-(aminooxymethyl)-phenyl glyoxylate O-methyloxime in 5 ml MeOH and 0.5 ml acetic acid catalyst. After 4 hours the mixture was worked up to give a yellow oil with a small amount of solid. The material washed with ether/hexane and filtered to give product in the filtrate. After removal of the solvent in vacuuo was isolated 1.7 g of methyl 2-[2-((((1-methyl-3-(2',3',6'-trichloro-phenyl)-trans-2-propenylidene)amino)oxy)methyl)phenyl]-2-methoxyimino-acetate as a yellow oil in a 54:46 A:B isomer ratio.(E,E,E:Z,E,E) and 90.7% isolated yield (80% chemical purity by GLC). NMR (300 MHz $^1$H CDCl$_3$): 2.08(d, 3H); 3.85(d, 3H); 4.04(d, 3H); 5.06(d, 2H); 6.7–7.6(m, 8H).

EXAMPLE 6

Preparation of E and Z imine isomers: (E,E,E) and (Z,E,E) of N-Methyl 2-[2-((((1-methyl-3-(2',3',6'-trychlorophenyl)-trans-2-propenylidene)amino)oxy)methyl)-phenyl]-2-methoxyiminoacetamide (Compounds 3.17A and 3.17B of Table 3).

Using the method of Example 2: 1.4 g (54:46 A:B isomer ratio) of (E and Z, E,E) methyl 2-[2-((((1-methyl-3-(2',3',6'-tri-chlorophenyl)-trans- 2-propenylidene)amino)oxy) methyl)phenyl]-2-methoxyiminoacetate (3.0 mmole, 80% purity) in 10 ml MeOH, 1.2 g(15.0 mmole) 40% aqueous methyl amine, and was heated 1.5 hours at reflux and worked up. A crude product (53:47 A:B isomer ratio of 65% chemical purity) as an oil was chromatographed on silica with 2:3 ethyl acetate/hexane followed by trituration with ether/hexane to afford both both isomer A (E,E,E) and isomer B (Z,E,E) of N-Methyl 2-[2-((((1-methyl-3-(2',3',6'-trichlorophenyl)-trans-2-propenylidene)amino)oxy) methyl)-phenyl]-2-methoxyiminoacetamide as solids: 180 mg of isomer-A (E,E,E) mp. 87–92° C. and 180 mg of isomer-B (Z,E,E) mp. 131–133° C., as off-white solids in an overall 32.0% isolated yield.

NMR isomer-A (300 MHz $^1$H CDCl$_3$): 2.08(s, 3H); 2.90(d, 3H); 3.96(s, 3H); 5.08(s, 2H); 6.7–7.5(m, 8H).

NMR isomer-B (300 MHz $^1$H CDCl$_3$): 2.1(s, 31H); 2.83(d, 3H); 3.90(s, 3H); 5.03(s, 2H); 6.7–7.5(m, 8H).

EXAMPLE 7

Preparation of E/Z imine isomers: (E,E,E) and (Z,E,E) of Methyl 2-[2-((((1-methyl-3-(2',6'-dichlorophenyl)-trans-2-propenylidene)amino)oxy)methyl)-phenyl]-2-methoxyiminoacetate (Compounds 2,16,2.16A and 2.16B of Table 2).

Preparation of trans 4-(2,6-dichlorophenyl)-3-buten-2-one

In a 250 ml single neck flask was charged 10 g (57 mmoles, 1.0 eq) of 2,6-dichlorobenzaldehyde dissolved in 100 ml of acetone. To this was added 2.28 g (5.7 mmoles, 0. 10eq.) of a 10% aqueous sodium hydroxide solution, dropwise and during the course of addition, temperature was kept no higher than 25°C., while the mixture was agitated continuously for 2 h. To the mixture was added 50 ml of water, followed by 100 ml of ethyl acetate, the phases were separated and the organic phase was washed with water three times and then dried, and concentrated to afford of (E)-4-(2,6-dichlorophenyl)-3-buten-2-one as a faintly yellow oil which was used directly in the following procedure. NMR (300 MHz $^1$H CDCl$_3$): 2.43 (s, 3H); 6.80(d, 1H); 7.18–7.3(m, 3H); 7.6(d, 1H).

Preparation of trans-1-(2.6-dichlorophenyl)-3-butene-2-one-2-oxime

In a 250 ml single neck flask was charged 12.5 g (57 mmoles, 1.0 eq.) of trans-4-(2,6-dichlorophenyl)-3-buten-2-one and 11.9 g (0.171 moles, 3.0 eq) of hydroxylamine hydrochloride and 19.67 g of potassium carbonate (0.143 moles, 2.5 eq) and 100 ml of ethanol. The reaction mixture was stirred at for 5 hours. The reaction mixture was concentrated, diluted with water (50 ml), and then extracted with ethyl acetate (2×50 ml). The organic phase was dried and concentrated, to obtain 7.6g of trans-1-(2,6-dichlorophenyl)-3-butene-2-one-2-oxime (E/Z mixture of oximes) as an oil in 58.2% yield.

Preparation of E/Z imine isomers: (E,E,E) and (Z,E,E) of Methyl 2-[2-((((1-methyl-3-(2',6'-dichlorohenyl)-trans-2-propenylidene)amino)oxy)methyl-phenyl]-2-methoxyiminoacetate using methyl 2-(2-bromomethylphenyl)-2-methoxyiminoacetate In a 100 ml single neck flask was charged 2.2 g of trans-1-(2,6-dichlorophenyl)-3-butene-2-one 2-oxime (E/Z mixture of oximes) (9.60 mmoles, 1.0 eq) in 20 ml of N,N-dimethylformamide to which was added 2.73 g (9.6mmoles, 1.0 eq) of methyl 2-(2-bromomethylphenyl)-

2-methoxyiminoacetate in 10 ml of DMF. When the reagents were dissolved, 0.58 g of NaOH (14.4 mmoles, 1.5eq.) was added. The reaction mixture changed to dark brown and was stirred continuously overnight at room temperature. The reaction mixture was poured into 100 ml of water, extracted with 150 ml of ethyl acetate, washed with 3×50 ml of water, dried and concentrated, to obtain the crude product. This was subjected to silica gel column chromatography, using a 1:8 mixture of ethyl acetate and hexane as the eluting solution and afforded both isomer A (E,E,E) and isomer B (Z,E,E) of methyl 2-[2-((((1-methyl-3-(2',6'-dichlorophenyl)-trans-2-propenylidene)amino)-oxy)methyl)-phenyl]-2-methoxyiminoacetate as oils: 600 mg of isomer-A (E,E,E) as a pink oil and 600 mg of isomer-B (Z,E,E) as a yellowish oil, in an overall 28.0% isolated yield. NMR isomer-A (300 MHz $^1$H CDCl$_3$): 2.08(s, 3H); 3.86, (s,3H); 4.04(s, 3H); 5.09(s, 2H); 6.84–6.86(ABq,2H), 7.1–7.7(m, 7H). NMR isomer-B (300 MHz $^1$H CDCl$_3$): 2.10(s, 3H); 3.78, (s,3H), 3.98(s, 3H); 5.03(ABq, 2-H); 6.7–7.6(m, 9H).

Preparation of E/Z imine isomers: (E and Z, E,E) and (E,E,E) of Methyl 2-[2-((((1-methyl-3-(2',6'-dichlorophenyl)-trans-2-propenylidene)amino)oxy)methyl)-phenyl]-2-methoxyiminoacetate using the Method of Example 1 Step 2 followed by Isomerization Using the method of Example 1 step 2: To 2.17 g of (10 mmole) trans-4(2,6-dichlorophenyl)-3-buten-2-one in 75 ml MeOH was added 2.38 g (10 mmole) methyl (E)-2-(aminooxymethyl)-phenyl glyoxylate O-methyloxime and stirred at reflux with monitoring by tlc (3:1 Hexane:EtOAc). After 3 hours workup gave an orange oil as a 70:30 isomer A:B which was used directly in Example 8. The procedure was repeated with 22.4 g (0.10 mole) trans-4-(2,6-dichlorophenyl)3-buten-2-one in 400 ml MeOH to which was added 29.34 g (0.123 mmole, 1.18 eq.) methyl (E)-2-(aminooxymethyl)-phenyl glyoxylate O-methyloxime and stirred overnight at room temperature. GLC indicated 83% product in a 1:1.2 ratio of isomer A:B. The reaction was heated at reflux with monitoring by GLC and when the ratio was 1:1 isomer A:B the reaction was cooled to room temperature. A white solid formed which was filtered and provided 16.16 g (57.9% yield) of 90% pure isomer A (E,E,E).mp 130–133° C. The filtrate which contained a 1:2.76 ratio of isomer A:B in 73% chemical purity was concentrated and CH$_2$Cl$_2$ was added followed by 5 ml of 10% HCL. The reaction mixture was stirred overnight after which GLC showed 4.63:1 ratio of isomer A:B in 70.4% chemical purity. The solvent was removed and to the residue was added methanol after which a light yellow solid formed (11.75 g) which was 9:1 isomer A (E,E,E): B (Z,E,E).

EXAMPLE 8

Preparation of E and Z imine isomers: (E,E,E) and (Z,E,E) of N-Methyl 2-[2-((((1-methyl-3-(2'3',6'-trichlorophenyl)-trans-2-propenylidene)amino)oxy) methyl)-phenyl]-2-methoxyiminoacetamide (Compounds 3.16, 3.16A and 3.16B of Table 3).

Isomer A and Isomer B of Example 7 were treated using the method of Ex.2: In a 100 ml round bottom flask was added 0.50 g of isomer A (E,E,E) methyl 2-[2-((((1-methyl-3-(2'',6'-dichlorophenyl)-trans-2-propenylidene)amino)oxy)methyl)-phenyl]-2-methoxyiminoacetate (1.15 mmole in 20 ml MeOH, and 0.7 g (9 mmole) 40% aqueous methyl amine was added. The mixture was heated at reflux for 26 h and worked up by removing the solvent, adding EtOAC and washing with water. The crude product as an oil was chromatographed on silica with 1:2 ethyl EtOAc:hexane to provide 200 mg of (E,E,E) N-methyl 2-[2-((((1-methyl-3-(2', 6'-dichlorophenyl)-trans-2-propenylidene)amino)oxy) methyl)-phenyl]-2-methoxyiminoacetamide as an oil which crystallized on standing, mp 127–129° C. (40% isolated yield).

NMR isomer-A (300 MHz $^1$H CDCl3): 2.08(s, 3H); 2.89–2.91(d, 3H); 3.96(s, 3H); 5.08(s, 2H); 6.84–6.87(ABq, 2M); 7.1–7.5(m, 7H).

Isomer B (500 mg) from Example 7 was treated as above. The crude product as an oil was chromatographed on silica with 1:3 ethyl EtOAc:hexane to provide 100 mg of (Z,E,E) N-methyl 2-[2-((((1-methyl-3-(2',6'-dichlorophenyl)-trans-2-propenylidene)amino)oxy)methyl)phenyl]-2-methoxyiminoacetamide as an oil. (20% isolated yield).

NMR isomer-B (300 MHz $^1$H CDCl$_3$): 2.11(s, 3H); 2.82–2.84(d, 3H); 3.89(s, 3H); 5.04(s, 2H); 6.8–7.5(m, 9H).

The 70:30 isomer A:B of Example 7 was used directly in the method of Example 2. In a 100 ml round bottom flask was added 6.85 g (15.8 mmole) of a 7:3 isomer A:B (E,E,E:Z,E,E) mixture of methyl 2-[2-((((1-methyl-3-(2'',6'-dichlorophenyl)-trans-2-propenylidene)amino)oxy)methyl) phenyl]-2-methoxyiminoacetate (1.15 mmole) in 60 ml MeOH, and 6.86 g (88.5 mmole, 5.6 eq.) of 40% aqueous methyl amine was added. The reaction mixture was heated at reflux for 3 h and worked up by removing the solvent, adding EtOAC and washing with water. Removal of the solvent provided 3.74 g of a tacky yellow solid (54.4% yield) in a 70:30 isomer A:B as determined by the integration of the NMR signals (300 MHz $^1$H CDCl$_3$) of the singlets at the chemical shifts of 3.89 and 3.96; 5.04 and 5.08 ppm.

The 90:10 isomer A:B of Example 7 (32 g, 74 moles) and the sample prepared from isomerization (16.4 g, 38 mmol) was used directly in the method of Example 2 and provided a 23.4 g (73.2% yield) and 12.97 g (78.7% yield), respectively, each in a 95:5 isomer A:B of Compound 3.16, mp. 129–131° C.

EXAMPLE 9

Physical property data and isomer A and B isomer ratios are provided in Table 7 for typical examples of Tables 1 to 6 and are illustrative of the present invention

TABLE 7

| Compd # | Isomer(s) | A:B isomer ratio | Physical Property mp )° C.) |
|---|---|---|---|
| 1.16A | A | | oil |
| 2.16A | A | | oil |
| 2.16B | B | | oil |
| 2.17 | A + B | 54:46 | oil |
| 2.22A | A | | 97–100 |
| 2.30 | A + B | 72:28 | 105–116 |
| 2.87 | A + B | 70:30 | 110–116 |
| 2.94 | A + B | 56:44 | 84–93 |
| 3.16A | A | | 127–129 |
| 3.16B | B | | oil |
| 3.16 | A + B | 70:30 | resin |
| 3.17A | A | | 87–92 |
| 3.17B | B | | 131–133 |
| 3.22A | A | | 79–82 |
| 3.22B | B | | 129–132 |
| 3.30 | A + B | 72:28 | 130–136 |
| 3.87 | A + B | 70:30 | oil |
| 3.94 | A + B | 56:44 | 109–128 |

EXAMPLE 10

Proton NMR data (300 MHz) are provided in Table 8 for typical examples of Tables 1 to 6 and are illustrative of the present invention*

TABLE 8

| Compd # | Proton NMR δ (chemical shifts rel. to TMS) |
|---|---|
| 1.16A | 2.2(s, 3H); 3.69, (s,3H), 4.04(s, 3H); 5.09(s, 2H); 6.84–6.86(ABq, 2H), 7.1–7.7(m, 7H). |
| 2.16A | 2.08(s, 3H); 3.86, (s,3H), 4.04(s, 3H); 5.09(s, 2H); 6.84–6.86(ABq, 2H), 7.1–7.7(m, 7H). |
| 2.16B | 2.10(s, 3H); 3.78, (s,3H), 3.98(s, 3H); 5.03(ABq, 2H); 6.7–7.6(m, 9H). |
| 2.17 | 2.08(d, 3H); 3.85(d, 3H); 4.04(d, 3H); 5.06(d, 2H); 6.7–7.6(m, 8H). |
| 2.22A | 2.05(s, 3H), 3.86(s, 3H); 4.04(s, 3H); 5.08(s, 2H); 6.8–7.5(m, 9H) |
| 2.30 | 2.06(d, 3H), 3.85(m, 12H); 4.03(d, 3H); 5.06(d, 2H), 6.13(s, 2H); 7.1–7.6(m, 6H) |
| 2.87 | 2.07(d, 3H); 3.86(d, 3H); 4.02(d, 3H); 5.09(d, 2H); 7–7.6(m, 9H). |
| 2.94 | 2.05(d, 3H); 3.8(d, 3H); 4:02(d, 3H); 5.03(d, 2H); 6.8–7.6(m, 10H) |
| 3.16A | 2.08(s, 3H); 2.89–2.91(d, 3H); 3.96(s, 3H); 5.08(s, 2H); 6.84–6.87(ABq, 2H); 7.1–7.5(m, 7H). |
| 3.16B | 2.11(s, 3H); 2.82–2.84(d, 3H); 3.89(s, 3H); 5.04(s, 2H); 6.8–7.5(m, 9H). |
| 3.16 | 2.08 and 2.11(s, 3H); 2.82–2.84 and 2.89–2.91(d, 3H); 3.89 andand 3.96(s, 3H); 5.04(s, 2H) and 5.08(s, 2H); 6.8–7.5(m, 9H). |
| 3.17A | 2.08(s, 3H); 2.90(d, 3H); 3.96(s, 3H); 5.08(s, 2H); 6.7–7.5(m, 8H). |
| 3.17B | 2.1(s, 3H); 2.83(d, 3H); 3.90(s, 3H); 5.03(s, 2H); 6.7–7.5(m, 8H).. |
| 3.22A | 2.05(s, 3H); 2.91(d, 3H); 3.96(s, 3H); 5.08(s, 2H); 6.7–7.5 (m, 9H) |
| 3.22B | 2.07(s, 3H); 2.86(d, 3H); 3.92(s, 3H); 5.05(s, 2H); 6.7–7.7(m, 9H) |
| 3.30 | 2.06(d, 3H); 2.9(dd, 3H); 3.8(m, 9H); 3.9(d, 3H); 5.05(d, 2H); 6.1(s, 2H); 6.7(m, 1H); 7.1–7.6(m, 6H) |
| 3.87 | 2.08(d, 3H); 3.85(d, 3H); 4.04(d, 3H); 5.06(d, 2H); 6.7–7.6(m, 8H). |
| 3.94 | 2.05(d, 3H); 2.87(dd, 3H); 3.93(d, 3H); 5.06(d, 2H); 6.7–7.6(m, 11H) |

*NMR data for compounds designated by A or B are data for one single stereoisomer for $R_2C=N-O$. Compounds without designation are a mixture of stereoisomers and the data provided is for the major isomer except for 3.16 which indicates the chemical shifts of both isomers.

$^1$HNMR spectra were recorded, using $CDCl_3$. Following codes were used: s=singlet d=doublets, t=triplets, m=multiplets, br=broad peak

EXAMPLE 11

Numerous compounds of this invention were tested for fungicidal activity in vivo against the diseases described below. The compounds were dissolved in a 1:1 mixture of acetone and methanol and then diluted with a 2:1:1 mixture of water, acetone and methanol (by volume) to achieve the appropriate concentration. The solution was sprayed onto plants and allowed to dry for two hours. The plants were then inoculated with fungal spores. Each test utilized control plants which were sprayed with the appropriate solvent and inoculated. For these protective tests, the plants were inoculated one day after treating the plants with the compounds of this invention. The remainder of the technique of each of the tests is given below along with the results for various compounds described herein by the Compound # against the various fungi at a dose of 150 grams per hectare. The results are percent disease control as compared to the untreated check, wherein one hundred was rated as complete disease control and zero as no disease control. The application of the test fungal spores to the test plants was as follows:

Wheat Leaf Rust (WLR)

*Puccinia recondita* (f. sp. tritici) was cultured on 7-day old wheat plants (cv. Fielder) over a 12-day period in the greenhouse. Spores were collected from the leaves by settling on aluminum foil. The spores were cleaned by sieving through a 250-micron opening screen and stored dry. The dried spores were used within one month. A spore suspension was prepared from dry uredia by adding 20 mg (9.5 million spores) per ml of Soltrol oil. The suspension was dispensed into gelatin capsules (0.7 ml capacity) which attach to the oil atomizers. One capsule is used per flat of twenty 2-inch square pots of 7-day old plants, cultivar Fielder. After waiting for at least 15 minutes for the oil to evaporate from the wheat leaves, the plants were placed in a Dew Chamber for 24 hours. The plants were then placed in the greenhouse and evaluated after 12 days for disease.

Wheat Leaf Blotch (SNW)

Cultures of *Septoria nodorum* was maintained on Czapek-Dox V-8 juice agar plates in an incubator at 20° C. with alternating periods of 12 hours of light and 12 hours of darkness for 2 weeks. A water suspension of the spores was obtained by shaking the portion of the plate with fungal material in deionized water and filtering through cheesecloth. The spore-containing water suspension was diluted to a spore concentration of $3.0\times10^6$ spores per ml. The inoculum was dispersed by a DeVilbiss atomizer over one-week old wheat plants (cv. Fielder) which had been previously sprayed with the fungicide compound. The inoculated plants were placed in a Dew Chamber at 20° C. with alternating 12 hours of light and 12 hours of darkness for 4 days. The inoculated seedlings were then moved to a controlled environment room at 20° C. and 80% humidity for 2 days. Disease control values were recorded as percent control.

Wheat Powdery Mildew (WPM)

*Erysiphe graminis* (f. sp. tritici) was cultured on wheat seedlings (cv. Fielder) in a controlled temperature room at 18° C. Mildew spores were shaken from the culture plants onto 7-day old wheat seedlings which had been previously sprayed with the fungicide compound. The inoculated seedlings were kept in a controlled temperature room at 18° C. and subirrigated. The percent disease control was rated 7 days after the inoculation. Disease control values were recorded as percent control.

Cucumber Powdery Mildew (CPM)

*Sphaerotheca fulginea* was maintained on cucumber plants (cv. Bush Champion hybrid) in the greenhouse. Inoculum was prepared by placing five to ten heavily mildewed leaves in a glass jar with 500 ml of water containing 1 drop of Tween 80 (polyoxyethylene monooleate) per 100 ml. After shaking the liquid and leaves, the inoculum was filtered through cheese cloth and misted onto the plants with a squirt bottle mister. The spore count was 100,000 spores per ml. The plants were then placed in the greenhouse for infection and incubation. The plants were scored seven days after inoculation. Disease control values were recorded as percent control.

Tomato Late Blight (TLB)

Cultures of *Phytophthora infestans* were maintained on green pea-amended agar for two to three weeks. The spores were washed from the agar with water and dispersed with a DeVilbiss atomizer over the leaves of 3-week old Patio hybrid tomato plants which had been previously treated with compound of -the present invention. The inoculated plants were placed in a Dew Chamber at 20° C. for 24 hours for infection. The plants were then removed to a controlled environment room at 20° C. and 90% humidity. The plants were scored for disease control after five days.

Grape Downy Mildew (GDM)

*Plasmopara viticola* was maintained on leaves of grape plants (cv. Delaware) in a controlled temperature chamber at 20° C. in humid air with moderate light intensity for 7 to 8 days. A water suspension of the spores from infested leaves was obtained and the spore concentration was adjusted to about $3 \times 10^5$ per ml of water. Delaware grape plants were inoculated by spraying the underside of leaves with a De Vilbiss atomizer until small drops were observed on the leaves. The inoculated plants were incubated in a Dew Chamber for 24 hours at 20° C. The plants were then removed to a controlled environmental room at 20° C. and 90% humidity. Disease control values were recorded as percent control seven days after inoculation.

Rice Blast (RB)

Cultures of *Pyricularia oyrzae* were maintained on potato dextrose agar for two to three week. The spores were washed from the agar with water containing 1 drop of Tween 80 per 100 ml. After filtering the spore suspension through two layers of cheese cloth, the spore count was adjusted to $5 \times 10^5$ per ml of water. The spore suspension was sprayed onto 12-day old rice plants (cv. M-201) using a De Vilbiss atomizer. The inoculated plants were placed in a totally dark Dew Chamber 20° C. for 36 hours to allow for infection. After the infection period the plants were placed in the greenhouse. After 6 days, the plants were scored for disease control. Disease control values were recorded as percent control.

Cucumber Downy Mildew (CDM)

The cultures of *Pseudoperonospora cubensis* were maintained on cucumber plants. Leaves showing excellent sporulation were frozen in glass jars at −40° C. After extracting the spores by shaking the leaves in water, the lower surface of the treated cucumber leaves were sprayed with a spore concentration of 100,000 spores per ml of water. The cucumber plants were placed in a Dew Chamber at 20° C. for 24 hr. After this infection period, the plants were placed in a growth chamber at 20° C. and 90% humidity for 5 days. After severe infection was observed, the leaves were examined for disease development. Disease control values were recorded as percent control.

Cucumber Anthracnose (CA)

The fungal pathogen *Colletotrichum lagenarium* was cultured on potato dextrose agar (PDA) in the dark at 22° C. for a period of 8 to 14 days. Spores of *C. lagenarium* were removed from the PDA plates by flooding the plate surface with distilled water, amended with 0.5% v/w of yeast extract. The upper surface of the fungal colony was scraped with a blunt plastic instrument until most of the spores were released into the aqueous environment. The spore suspension was filtered though cheesecloth, and the spore count was adjusted by adding more water, containing the yeast extract, until $3.0 \times 10^6$ spores per ml of water was achieved. The chemically-treated cucumber plants were 15-days old (cv. Bush Champion hybrid). The upper leaf surface of the plants were sprayed with the spore suspension until runoff, using a hand-held pump spray bottle. The plants were placed in a fluorescent-lighted mist chamber (12 hr light, 12 hr dark) for 48 hours. After that infection period, the plants were placed in a growth chamber for 3 days at 25° C. and 80% humidity. The treated plants were then evaluated for disease control. Disease control values were recorded as percent control. Chemically-treated sweet bell pepper plants were 19-days old, cultivar California Wonder. The entire leaf surface of the plants were sprayed with the spore suspension until runoff, using a De Vilbiss atomizer. The plants were placed in a low light Dew Chamber (12 hr light, 12 hr dark) at 22 C for 3 or 4 days. The treated plants were then evaluated for disease control. Disease control values were recorded as percent control.

Botrytis of Sweet Bell Peppers (BOT)

The fungal pathogen *Botrytis cinerea* was cultured on potato dextrose agar (PDA) under fluorescent lights (12 hr on, 12 hr off) for a period of 2 to 3 weeks. Spores of *B. cinerea* were removed from the PDA plates by flooding the plate surface with distilled water, amended with 0.5% v/w of yeast extract. The upper surface of the fungal colony was scraped with a rubber instrument until most of the spores were released into the aqueous environment. The spore suspension was filtered though cheesecloth, and the spore count was adjusted by adding more water, containing the yeast extract, until $3.0 \times 10^6$ spores per ml was achieved. Chemically-treated sweet bell pepper plants were 19-days old, cultivar California Wonder. The entire leaf surface of the plants were sprayed with the spore suspension until runoff, using a De Vilbiss atomizer. The plants were placed in a low light Dew Chamber (12 hr light, 12 hr dark) at 22 C for 3 or 4 days. The treated plants were then evaluated for disease control. Disease control values were recorded as percent control.

Tomato Early Blight (TEB)

Cultures of *Alternaria solani* were grown on V-8 juice agar plates at room temperature under fluorescent lights (12 hr light, 12 hr dark) for 2 weeks. A suspension of the spores was obtained flooding the surface of the agar plate with a 0.5% solution of yeast extract in distilled water. The surface of the agar plate was scraped lightly with a blunt plastic instrument to release the spores into the liquid. The spore suspension was filtered through cheesecloth, and the spore concentration was adjusted to approximately 80,000 spores per ml. Tomato plants (cv. Patio hybrid) were approximately 18-days old at time of treatment with experimental compounds. Following treatment, the plants were placed in the greenhouse for 1 day. After this period, the plants were inoculated with freshly prepared spore suspension using a De Vilbiss atomizer. The spore suspension was applied to the upper surface of the leaves. After inoculation, the plants were placed in a Dew Chamber at 20° C. for 24 hr to allow for infection. The plants were then transferred to a growth chamber at 22° C. and 80% humidity for three days. Disease control values were recorded a percent control.

When tested against wheat leaf rust at 150 grams per hectare compounds 1.16A, 2.16A, 2.22A, 2.94, 3.16A, 3.16B, 3.17A, 3.17B, 3.22A, 3.22B, 3.87, and 3.94 exhibited 95% or better control.

When tested against wheat leaf blotch at 150 grams per hectare compounds 1.16A, 3.16A, and 3.22A exhibited 90% or better control.

When tested against wheat powdery mildew at 150 grams per hectare compounds 1.16A, 2.16B, 2.22A, 2.94, 3.16A, 3.16B, 3.17A, 3.22A, 3.22B, 3.87, and 3.94 exhibited 90% or better control.

When tested against cucumber powdery mildew at a dose of 150 grams per hectare compounds 2.16A, 2.22A, 2.94, 3.16, 3.16A, 3.17A, 3.17B, 3.22A, 3.22B, 3.87, and 3.94 exhibited 100% control.

When tested against tomato late blight at 150 grams per hectare compounds 1.16A, 2.16A, 3.16, 3.16A, 3.17A, 3.22A, and 3.94 exhibited 90% or better control.

When tested against rice blast at 150 grams per hectare compounds 1.16A, 2.16A, 2.17, 2.22A, 2.94, 3.16, 3.16A, 3.16B, 3.17A, 3.17B, 3.22A, 3.22B, 3.87, and 3.94 exhibited 90% control.

When tested against cucumber downy mildew at 150 grams per hectare compounds 1.16A, 2.17, 2.22A, 2.94, 3.16A, 3.17A, 3.17B, 3.22A, and 3.22B exhibited 100% control.

When tested against cucumber anthracnose at 150 grams per hectare compounds 1.16A, 3.16, 3.16A, 3.16B, 3.22A, 3.87 and 3.94 exhibited 95% or better control.

When tested against sweet bell pepper botrytis at 150 grams per hectare 2.16A and 3.16A exhibited 90% or better control.

When tested against tomato early blight at 150 grams per hectare compounds 2.30, 2.87, 2.94, 3.16, 3.16A, 3.16B, 3.30, 3.87 and 3.94 exhibited 90% or better control.

The compounds of this invention are useful as agricultural fungicides and, as such, can be applied to various loci such as the seed, the soil or the foliage of plants to be protected.

The compounds of this invention can be applied as fungicidal sprays by methods commonly employed, such as conventional high-volume hydraulic sprays, low-volume sprays, air-blast spray, aerial sprays and dusts. The dilution and rate of application will depend upon the type of equipment employed, the method of application, plants to be treated and diseases to be controlled. Generally, the compounds of this invention will be applied in amount of from about 0.005 kilogram to about 50 kilograms per hectare and preferably from about 0.025 to about 25 kilograms per hectare of the active ingredient.

As a seed protectant, the amount of toxicant coated on the seed is usually at a dosage rate of from about 0.05 to about 20 grams, preferably from about 0.05 to about 4 grams, and more preferably from about 0.1 to about 1 grams per hundred kilograms of seed. As a soil fungicide the chemical can be incorporated in the soil or applied to the surface usually at a rate of from about 0.02 to about 20 kilograms, preferably from about 0.05 to about 10 kilograms, and more preferably from about 0.1 to about 5 kilograms per hectare. As a foliar fungicide, the toxicant is usually applied to growing plants at a rate of from about 0.01 to about 10 kilograms, preferably from about 0.02 to 5 kilograms, and more preferably from about 0.25 to about 1 kilograms per hectare.

Inasmuch as the compounds of this invention display fungicidal activity, these compounds can be combined with other known fungicides to provide broad spectrum activity. Suitable fungicides include, but are not limited to, those compounds listed in U.S. Pat. No. 5,252,594. Other known fungicides which an be combined with the compounds of this invention are dimethomorph, cymoxanil, thifluzamide, furalaxyl, ofurace, benalaxyl, oxadixyl, propamocarb, cyprofuram, zoxamide, fenpiclonil, fludioxonil, pyrimethanil, cyprodinil, triticonazole, fluquinconazole, metconazole, spiroxamine, carpropamid, azoxystrobin, kresoxim-methyl, metominostrobin and trifloxystrobin.

The compounds of this invention can be advantageously employed in various ways. Since these compounds possess broad spectrum fungicidal activity, they can be employed in the storage of cereal grain. These compounds can also be employed as fungicides in cereals including wheat, barley and rye, in rice, peanuts, beans and grapes, on turf, in fruit, nut and vegetable orchards, and for golf course applications.

Examples of diseases against which the compounds of the invention are useful include helminthosporium of corn and barley, wheat and barley powdery mildew, wheat leaf and stem rusts, barley stripe and leaf rust, tomato early blight, tomato late blight, peanut early leaf spot, grape powdery mildew, grape black rot, apple scab, apple powdery mildew, cucumber powdery mildew, brown rot of fruits, botrytis, bean powdery mildew, cucumber anthracnose, wheat septoria nodorum, rice sheath blight and rice blast Compositions and formulations according to the present invention may also include known pesticidal compounds. This expands the spectrum of activity of the preparation and may give rise to synergism. Suitable insecticides known in the art include those listed in U.S. Pat. No. 5,075,471.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. If desired, adjuvants such as surfactants, stabilizers, antifoam agents and anti-drift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles. Wettable powders, pastes, flowables and emulsifiable concentrates are concentrated preparations which are diluted with water or oil before or during use. In such formulations, the compounds are extended with a liquid or solid carrier and, when desired, suitable surfactants are incorporated. Baits are preparations generally comprising a food or other substance attractive to insects, that includes at least one compound of the instant invention.

It is usually desirable, particularly in the case of foliar spray formulations, to include adjuvants, such as wetting agents, spreading agents, dispersing agents, stickers, adhesive and the like in accordance with agricultural practices. A listing of such adjuvants commonly used in the art, and a discussion of adjuvants, can be found in many references, such as in the John W. McCutcheon, Inc. publication "Detergents and Emulsifiers, Annual."

The active compounds of the present invention may be employed alone or in the form of mixtures with one another and/or with such solid and/or liquid dispersible carrier vehicles and/or with other known compatible active agents, especially plant protection agents, such as other insecticides, arthropodicides, nematicides, fungicides, bactericides, rodenticides, herbicides, fertilizers, growth-regulating agents, synergists.

In the compositions of the invention, the active compound is present in an amount substantially between about 0.0001 (1:999,999) -99 (99:1) % by weight. For compositions suitable for storage or transportation, the amount of active ingredient is preferably between about 0.5 (1:199) -90 (9:1) % by weight, and more preferably between about 1 (1:99) -75 (3:1) % by weight of the mixture. Compositions suitable for direct application or field application generally contain the active compound in an amount substantially between about 0.0001 (1:999,999) -95 (19:1) %, preferably between about 0.0005 (1:199,999) -90 (9:1) % by weight, and more preferably between about 0.001 (1:99,999) -75 (3:1) % by weight of the mixture. The composition can also be stated as a ratio of the compound to the carrier. In the present invention the weight ratio of these materials (active compound/carrier) can vary from 99:1 (99%) to 1:4 (20%) and more preferably from 10:1 (91%) to 1:3 (25%).

In general, the compounds of this invention can be dissolved in certain solvents such as acetone, methanol, ethanol, dimethylformamide, pyridine or dimethyl sulfoxide and such solutions can be diluted with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent to enhance dispersion of the compound in water. The concentration of the active ingredient in emulsifiable concentrates is usually from about 10% to about 90%, and in flowable emulsion concentrates, can be as high as about 75%.

Wettable powders suitable for spraying, can be prepared by admixing the compound with a finely divided solid, such as clay, inorganic silicate and carbonate, and silica and incorporating wetting agents, sticking agents, and/or dispersing agents in such mixtures. The concentration of active ingredients in such formulations is usually in the range of from about 20% to about 99%, preferably from about 40% to about 75%. A typical wettable powder is made by blending 50 parts of a compound of Formula I, 45 parts of a synthetic precipitated hydrated silicon dioxide and 5 parts of sodium lignosulfonate. In another preparation a kaolin type (Barden) clay is used in place of the synthetic precipitated hydrated silicon dioxide in the above wettable powder, and in another such preparation 25% of the silicon dioxide is replaced with a synthetic sodium silicoaluminate.

Dusts are prepared by mixing compounds of this invention with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

In addition to the aforementioned ingredients the preparations according to the invention may also contain other substances commonly used in preparations of this kind. For example, a lubricant, such as calcium stearate or magnesium stearate, may be added to a wettable powder or to a mixture to be granulated. Furthermore there may, for example, be added "adhesives" such as polyvinylalcohol-cellulose derivatives or other colloidal materials, such as casein, to improve the adherence of the pesticide to the surface to be protected.

We claim:
1. A compound of the formula:

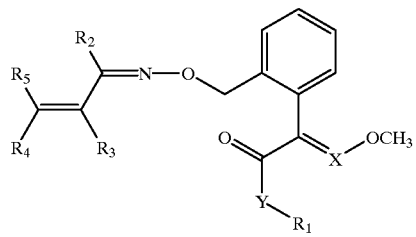

wherein X is N or CH; Y is O, S, or $NR_6$;

A is hydrogen, halo, cyano, $(C_1-C_{12})$alkyl, or $(C_1-C_{12})$alkoxy;

$R_1$ and $R_6$ are independently hydrogen or $(C_1-C_4)$alkyl;

$R_2$ is hydrogen, $(C_1-C_{12})$allyl, halo$(C_1-C_{12})$alkyl, $(C_3-C_7)$cycloalkyl, $(C_2-C_8)$alkenyl, halo$(C_2-C_8)$alkenyl, $(C_2-C_8)$alkynyl, halo$(C_2-C_8)$alkynyl, aryl, aralkyl, heterocyclic, or heterocyclic$(C_1-C_4)$alkyl;

$R_3$ is hydrogen or $(C_1-C_4)$alkyl;

$R_4$ and $R_5$ are independently hydrogen, $(C_1-C_4)$alkyl, aryl, aralkyl, aryl$(C_2-C_8)$alkenyl, aryl$(C_2-C_8)$alkynyl, heterocyclic, or heterocyclic$(C_1-C_4)$alkyl, wherein with each aryl, aralkyl, aryl$(C_2-C_8)$alkenyl, aryl$(C_2-C_8)$alkynyl, heterocyclic or heterocyclic$(C_1-C_4)$ alkyl the aryl or heterocyclic ring is substituted with from 2 to 5 substituents and wherein the positions on the aryl or heterocyclic ring adjacent to the ethylenic bond, are both substituted and wherein if one of $R_4$ and $R_5$ is hydrogen or $(C_1-C_4)$alkyl then the other of $R_4$ and $R_5$ is other than hydrogen or $(C_1-C_4)$alkyl;

and enantiomers, stereoisomers, and agronomically acceptable salts thereof.

2. The compound of claim 1 wherein X is CH, Y is O, $R_2$ is $(C_9-C_{12})$alkyl, and $R_3$ is hydrogen.

3. The compound of claim 2 wherein one of $R_4$ and $R_5$ is selected from the group consisting of 2,6-dihalophenyl, 2,3,6-trihalophenyl, 2,4,6-trihalophenyl, 2,3,4,6-tetrahalophenyl, 2,6-trihalomethylphenyl and 2,4,6-trihalomethylphenyl.

4. The compound of claim 3 wherein one of $R_4$ and $R_5$ is selected from the group consisting of 2,6-dichlorophenyl, 2,3,6-trichlorophenyl, 2,4,6-trichlorophenyl, 2,6-bis-trifluoromethylphenyl, 2-chloro-6-fluorophenyl, and 2,6-difluorophenyl.

5. The compound of claim 1 wherein X is N, Y is O or NH, $R_2$ is $(C_1-C_{12}$alkyl and $R_3$ is hydrogen.

6. The compound of claim 5 wherein one of $R_4$ and $R_5$ is selected from the group consisting of 2,6-dihalophenyl, 2,3,6-trihalophenyl, 2,4,6-trihalophenyl, 2,3,4,6-tetrahalophenyl, 2,6-trihalomethylphenyl and 2,4,6-trihalomethylphenyl.

7. The compound of claim 6 wherein one of $R_4$ and $R_5$ is selected from the group consisting of 2,6-dichlorophenyl, 2,3,6-dichlorophenyl, 2,4,6-chlorophenyl, 2,6-bis-trifluoromethylphenyl, 2-chloro-6-fluorophenyl, and 2,6-difluorophenyl.

8. The compound of claim 1 where the compound is N-Methyl 2-[2-((((1-methyl-3-(2',6'-dichlorophenyl)-trans-2-propenylidene)amino)oxy)methyl)-phenyl]-2-methoxyiminoacetamide.

9. A fungicidal composition for controlling phytopathogenic fungi which comprises an agronomically acceptable carrier and the compound of claim 1 wherein the ratio of the carrier to the compound is between 99:1 and 1:4.

10. A method for controlling phytopathogenic fungi which comprises applying the compound of claim 1 to the locus where control is desired, at a rate of from 0.005 to 50 kilograms per hectare.

* * * * *